US012715893B2

(12) United States Patent
Stappenbeck et al.

(10) Patent No.: US 12,715,893 B2
(45) Date of Patent: Aug. 25, 2026

(54) OXYSTEROL COMPOUNDS AND USES THEREOF

(71) Applicant: MAX BIOPHARMA, INC., Los Angeles, CA (US)

(72) Inventors: Frank Stappenbeck, Los Angeles, CA (US); Farhad Parhami, Los Angeles, CA (US); Feng Wang, Los Angeles, CA (US)

(73) Assignee: MAX BIOPHARMA, INC., Los Angeles, CA (US)

( * ) Notice: Subject to any disclaimer, the term of this patent is extended or adjusted under 35 U.S.C. 154(b) by 706 days.

(21) Appl. No.: 18/007,699

(22) PCT Filed: Jun. 4, 2021

(86) PCT No.: PCT/US2021/035973
§ 371 (c)(1),
(2) Date: Dec. 1, 2022

(87) PCT Pub. No.: WO2021/248049
PCT Pub. Date: Dec. 9, 2021

(65) Prior Publication Data

US 2023/0234982 A1 Jul. 27, 2023

Related U.S. Application Data

(60) Provisional application No. 63/035,597, filed on Jun. 5, 2020.

(51) Int. Cl.
*C07J 9/00* (2006.01)
*C07J 43/00* (2006.01)

(52) U.S. Cl.
CPC .............. *C07J 9/00* (2013.01); *C07J 43/003* (2013.01)

(58) Field of Classification Search
CPC ................................ C07J 9/00; C07J 43/003
See application file for complete search history.

(56) References Cited

U.S. PATENT DOCUMENTS

| | | | |
|---|---|---|---|
| 3,131,179 | A | 4/1964 | Hoffmann et al. |
| 4,229,447 | A | 10/1980 | Porter |
| 4,476,116 | A | 10/1984 | Anik |
| 4,596,795 | A | 6/1986 | Pitha |
| 4,755,386 | A | 7/1988 | Hsiao et al. |
| 5,011,692 | A | 4/1991 | Fujioka et al. |
| 5,017,381 | A | 5/1991 | Maruyama et al. |
| 5,116,817 | A | 5/1992 | Anik |
| 5,229,135 | A | 7/1993 | Philippon et al. |

(Continued)

FOREIGN PATENT DOCUMENTS

| | | |
|---|---|---|
| EP | 0477107 A1 | 3/1992 |
| EP | 0562849 A2 | 9/1993 |

(Continued)

OTHER PUBLICATIONS

Ansel, Howard C. et al. Pharmaceutical Dosage Forms and Drug Delivery Systems, 6th Edition. 1-7 (1995).

(Continued)

*Primary Examiner* — Kortney L. Klinkel
*Assistant Examiner* — Jackson J Hernandez
(74) *Attorney, Agent, or Firm* — Wilson Sonsini Goodrich & Rosati

(57) ABSTRACT

Described herein are compounds and pharmaceutical compositions containing such compounds for the modulation of Hedgehog signaling.

18 Claims, 9 Drawing Sheets

Conformational properties of sterols: Substitution and configuration at C-20 can favor extended or bent side chain conformation

(56) References Cited

U.S. PATENT DOCUMENTS

| | | | |
|---|---|---|---|
| 5,739,136 | A | 4/1998 | Ellinwood, Jr. et al. |
| 5,837,284 | A | 11/1998 | Mehta et al. |
| 5,840,329 | A | 11/1998 | Bai |
| 5,858,401 | A | 1/1999 | Bhalani et al. |
| 6,391,452 | B1 | 5/2002 | Antonsen et al. |
| 6,667,048 | B1 | 12/2003 | Lambert et al. |
| 6,960,563 | B2 | 11/2005 | Egbaria et al. |
| 7,897,588 | B2 | 3/2011 | Parhami |
| 8,022,052 | B2 | 9/2011 | Parhami et al. |
| 8,545,311 | B2 | 10/2013 | Shore et al. |
| 9,526,737 | B2 | 12/2016 | Parhami et al. |
| 9,637,514 | B1 * | 5/2017 | Stappenbeck et al. |
| 9,717,742 | B2 | 8/2017 | Parhami et al. |
| 10,869,875 | B2 * | 12/2020 | Stappenbeck et al. |
| 2005/0049230 | A1 | 3/2005 | Henrich et al. |
| 2006/0025393 | A1 | 2/2006 | Liao et al. |
| 2008/0020381 | A1 | 1/2008 | Henrich et al. |
| 2010/0034781 | A1 | 2/2010 | Parhami et al. |
| 2011/0008297 | A1 | 1/2011 | Parhami et al. |
| 2012/0309730 | A1 | 12/2012 | Parhami et al. |
| 2015/0118277 | A1 | 4/2015 | Parhami et al. |
| 2015/0140059 | A1 | 5/2015 | Parhami et al. |
| 2016/0159850 | A1 | 6/2016 | Parhami et al. |
| 2017/0114089 | A1 | 4/2017 | Stappenbeck et al. |
| 2017/0189420 | A1 | 7/2017 | Stappenbeck et al. |
| 2019/0314291 | A1 | 10/2019 | Besin et al. |
| 2020/0014722 | A1 | 1/2020 | Walters et al. |
| 2023/0364111 | A1 | 11/2023 | Parhami et al. |
| 2023/0381201 | A1 | 11/2023 | Parhami et al. |

FOREIGN PATENT DOCUMENTS

| | | | |
|---|---|---|---|
| GB | 869007 | A | 5/1961 |
| JP | H08268917 | A | 10/1996 |
| JP | 2009000103 | A | 1/2009 |
| JP | 2014076066 | A | 5/2014 |
| WO | WO-9303732 | A1 | 3/1993 |
| WO | WO-9521617 | A1 | 8/1995 |
| WO | WO-9809935 | A1 | 3/1998 |
| WO | WO-9958549 | A1 | 11/1999 |
| WO | WO-03030857 | A1 | 4/2003 |
| WO | WO-2004103320 | A2 | 12/2004 |
| WO | WO-2005020928 | A2 | 3/2005 |
| WO | WO-2006110490 | A2 | 10/2006 |
| WO | WO-2007028101 | A2 | 3/2007 |
| WO | WO-2007098281 | A2 | 8/2007 |
| WO | WO-2007103162 | A2 | 9/2007 |
| WO | WO-2008011071 | A2 | 1/2008 |
| WO | WO-2008115469 | A2 | 9/2008 |
| WO | WO-2009073186 | A1 | 6/2009 |
| WO | WO-2009108804 | A2 | 9/2009 |
| WO | WO-2010079594 | A1 | 7/2010 |
| WO | WO-2010088409 | A2 | 8/2010 |
| WO | WO-2011006087 | A1 | 1/2011 |
| WO | WO-2011025064 | A1 | 3/2011 |
| WO | WO-2011053048 | A2 | 5/2011 |
| WO | WO-2011073419 | A1 | 6/2011 |
| WO | WO-2011103175 | A2 | 8/2011 |
| WO | WO-2012024584 | A2 | 2/2012 |
| WO | WO-2013036835 | A1 | 3/2013 |
| WO | WO-2013169397 | A1 | 11/2013 |
| WO | WO-2013169399 | A1 | 11/2013 |
| WO | WO-2014020577 | A1 | 2/2014 |
| WO | WO-2014179756 | A1 | 11/2014 |
| WO | WO-2015168636 | A1 | 11/2015 |
| WO | WO-2017074957 | A1 | 5/2017 |
| WO | WO-2021248049 | A1 | 12/2021 |

OTHER PUBLICATIONS

Ansel, Howard C. et al. Pharmaceutical Dosage Forms and Drug Delivery Systems, Seventh Edition. Lippincott Williams & Wilkins (1999).

Arai et al., Synthesis of ponasterone A derivatives with various steroid skeleton moieties and evaluation of their binding to the ecdysone receptor of Kc cells. Steroids, 73:1452-1464 (2008).

Bannai et al, Studies on steroids Part 37 Synthesis of the four stereoisomers of 20,22-Epoxycholesterol Journal of the Chemical Society, Perkin Transactions 1 Organic and Bio-Organic. Chemistry (1972-1999), (19):2116-20 (1976).

Benelli et al, Cholesterol hydroxylations in adrenal cortex and testis of the thyroidectomized RAT Thyroid Research VIII. Proc. EighthInt. Thyroid Congr., Sydney, Australia, p. 327-30 (1980).

Burstein et al, Inhibition of the conversion of cholesterol to pregnenolone in bovine Adrenocortical preparations Steroids, 27(3):361-82 (1976).

Burstein et al., Reactions of 20-Hhrdoxylated steroids with bovine adernal tissue preparations. Steroids, 13(3):399-412 (1968).

Burstein et al, Substrate-induced difference spectra and cholesterol to pregnenolone conversation with adrenal heme protein P-450. Biochemistry, 11(4):573-7 (1972).

Chaudhuri et al, Stereochemistry of the addition reactions of Grignard reagents to 20-keto steroids.Synthesis of 17α,20α-Dihydroxycholesterol Journal of Organic Chemistry, 34(12):3759-3766 (1969).

Ciobanu et al., Synthesis and steroid sulphatase inhibitory activity of C19- and C21-steroidal derivatives bearing a benzyl-inhibiting group. Eur.J.Med.Chem., 36:659-671 (2001).

DiBussolo et al, Structural elucidation of sterols by reversed-phase liquid chromatography: I. Assignment of retention coefficients to various groups.Journal of Chromatographic Science, 20(5):193-202 (1982).

Duncan, J. L., Effects of streptolysin O on mammalian cells Pathog. Streptococci,Proc. VIIth Int. Symp. Streptococci and Streptococcal Diseases p. 56-57, Sep. 1978.

Gennaro, Alfonso R. Remington: Practice of The Science and Pharmacy, 19th Edition. Mack Publishing Company (1995).

Gennaro, Alfonso R. Remington: The Science and Practice of Pharmacy, 21st Edition. Mack Publishing Company (2005).

Greene, Theodora W, and Peter G M Wuts. Protective Groups in Organic Synthesis, 3rd Edition. John Wiley & Sons, Inc (1999).

Heer and Hoffmann, Uber Pyridyl-Steroide. I., Helvetica Chimica Acta, Chapter 214, p. 1804-1813 (1956).

Hochberg et al, Transient, reactive intermediates in the biosynthesis of pregnenolone from cholesterolInternational Congress Series (1973), (Endocrinol., Proc. Int. Congr., 4th, 1972), 273:808-13.

Hoover, John E. et al. Remington's Pharmaceutical Sciences. Mack Publishing Company 1-5 (1975).

Horie et al, Heme-linked spectral changes of the protein moiety of hemoproteins in the near ultraviolet region.Journal of Biochemistry, 97(1):281-293 (1985).

Janowski et al, An oxysterol signaling pathway mediated by the nuclear receptor LXRα.Nature, 383(6602):728-731 (1996).

Klinefelter et al, Effect of Luteinizing hormone deprivation in Situ on steroidogenesis of rat leydig cells purified by a multistep procedure. Biology of Reproduction, 36(3):769-83 (1987).

Korahani et al, Autoxidation of cholesterol fatty ac ids esters in solid state and aqueous dispersion.Lipids, 17(10):703-8 (1982).

Kusano et al., Antifungal properties of solanum alkaloids. Che. Pharm. Bull., 35(12):4862-4867 (1987).

Larock, Richard C. Comprehensive Organic Transformations: A Guide to Functional Group Preparations. VCH Publishers (1989).

"Liquid Dosage Forms." In: *Encyclopedia of Pharmaceutical Technology*, 2nd Ed., vol. 1, edited by James Swarbrick and James C. Boylan, New York: Marcel Dekker, Inc., pp. 754-757 (2002).

Liberman, Herbert A. and Leon Lachman. Pharmaceutical Dosage Forms: Parental Medications. Marcel Decker, New York 1-7 (1980).

March, Jerry. Advanced Organic Chemistry: Reactions, Mechanisms and Structure, 4th Edition. John Wiley & Sons (1992).

Morisaki et al, Stereochemical specificity at Carbon-20 and -22 of hydroxylated cholesterols for side-chain cleavage by adrenocortical cytochrome P-450scc. FEBS Letters, 72(2):337-40 (1976).

Myers et al., Hedgehog pathway modulation by multiple lipid binding sites on the Smoothened effector of signal response. Developmental Cell, 26:346-357 (2013).

Nachtergaele et al., Oxysterols are allosteric activators of the oncoprotein Smoothened. Nature Chemical Biology, 8:211 (2012). Published online at DOI:10.1038/NCHEMBIO.765.

(56) References Cited

OTHER PUBLICATIONS

Nedelcu et al., Oxysterol binding to the extracellular domain of Smoothened in Hedgehog signaling. Nature Chemical Biology. Published online Jul. 7, 2013 at: DOI:10:1038/INCHEMBIO.1290.
Nes and Varkey, (Z)-17(20)-Dehydrocholesterol.A new sterol with C-21 and C-22 spatially fixed.Journal of Organic Chemistry, 41(21):3429-2933 (1976).
Neyses et al, Cholesterol and its oxidized derivatives modulate the calcium channel in human red blood cells Journal of Hypertension, 2(Suppl. 3):489-92 (1984).
PCT Patent Application No. PCT/US2016/058708 International Preliminary Report on Patentability dated May 11, 2018.
PCT/US2016/058708 International Search Report and Written Opinion dated Jan. 17, 2017.
PCT/US2021/035973 International Invitation to Pay Additional Fees dated Aug. 19, 2021.
PCT/US2021/035973 International Search Report and Written Opinion dated Oct. 26, 2021.
Peng et al, Effects of oxygenated derivatives of cholesterol on cholesterol uptake by cultured aortic smooth muscle cells Artery, 13(3):144-64 (1985).
Pratt et al, Membrane sterols and the development of the preimplantation mouse embryo Journal of Embryology and Experimental Morphology, 60:303-19 (1980).
Saito et al, Lysis of platelets and erythrocytes by the incorporation of a unique oxygenated sterol: 22R-hydroxycholesterol. Journal of Membrane Biology, 83(1-2):187-191 (1985).
Shimada et al, Rapid modulation of platelet aggregation in plasma by oxygenated sterols. Journal of Applied Biochemistry, 6(3):151-55 (1984).
Singh, Shailesh K, and Venkatesh Naini. Dosage forms: Non-Parenteral. Encyclopedia of Pharmaceutical Technology, 2nd Edition 1:754-757 (2002).
Stappenbeck et al, Novel oxysterols activate the Hedgehog pathway and induce osteogenesis. Bioorganic & Medicinal Chemistry Letters, 22(18):5893-5897 (2012).
Tuckey et al, Kinetics of the incorporation of adrenal cytochrome P-450scc into phosphatidylcholine vesicles. Journal of Biological Chemistry, 257(16):9309-14 (1982).
U.S. Appl. No. 15/055,402 First Action Interview dated Aug. 17, 2016.
U.S. Appl. No. 15/055,402 Office Action mailed May 20, 2016.
U.S. Appl. No. 15/463,904 Office Action dated Aug. 9, 2018.
U.S. Appl. No. 15/463,904 Office Action dated Feb. 12, 2018.
U.S. Appl. No. 15/771,005 Office Action dated Feb. 21, 2020.
U.S. Appl. No. 15/771,005 Office Action dated Jun. 13, 2019.
Veldhuis et al, An inhibitory role for the protein kinase C pathway in ovarian steroidogenesis. Biochemical Journal, 239(3) :505-11 (1986).
Velgova et al, On Steroids. CXXVL. Further compounds with antisclerotization effect on *Pyrrhocoris apterus* L. Larvae; Structure and Activity correlations Collection of Czechoslovak Chemical Communications, 34(11):3354-3376 (1969).
Viola et al, Side chain degradation and microbial reduction of different steroids by *Aspergillus aureogulgens*. Journal of Steroid Biochemistry, 19(4):1451-8 (1983).
Voigt et al, Massenspektrometrie von 20-Pyridylsteroiden. Pharmazie, 30(4):213-216 (1975) (In German, no English language translation provided).
Watanabe et al., Stereoselective synthesis of (22R)- and (22S)-castasterone/ponasterone A hybrid compounds and evaluation of their molting hormone activity. Steroids, 69:483-491 (2004).
Stappenbeck et al.: Inhibition of Non-Small Cell Lung Cancer Cells by Oxy210, an Oxysterol-Derivative that Antagonizes TGFß and Hedgehog Signaling. Cells. 8:1-26 (2019).
Wang et al.: Inhibition of Hedgehog Signaling in Fibroblasts, Pancreatic, and Lung Tumor Cells by Oxy186, an Oxysterol Analogue with Drug-Like Properties. Cells. 8:1-17 (2019).

* cited by examiner

Conformational properties of sterols: Substitution and configuration at C-20 can favor extended or bent side chain conformation 2-D drawings

Compound 10

Compound 13

Compound 5

Conformational drawings

Compound 10

Compound 13

Compound 5

X-ray structures

Compound 10, extended side chain

Compound 13, bent side chain

Compound 5, extended side chain

- All compounds are C-20 alcohols in the R-configuration.

Compound 1

Compound 2

Compound 5

Compound 6

Compound 3

Compound 4a

Compound 4b

Compound 7

Compound 5, extended side chain

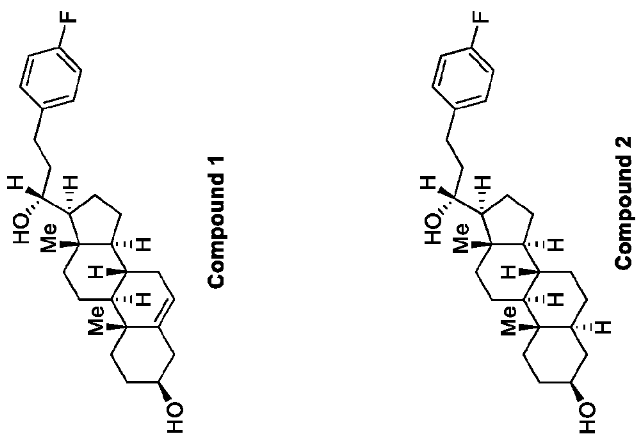
Compound 1
Compound 2
Figure 5
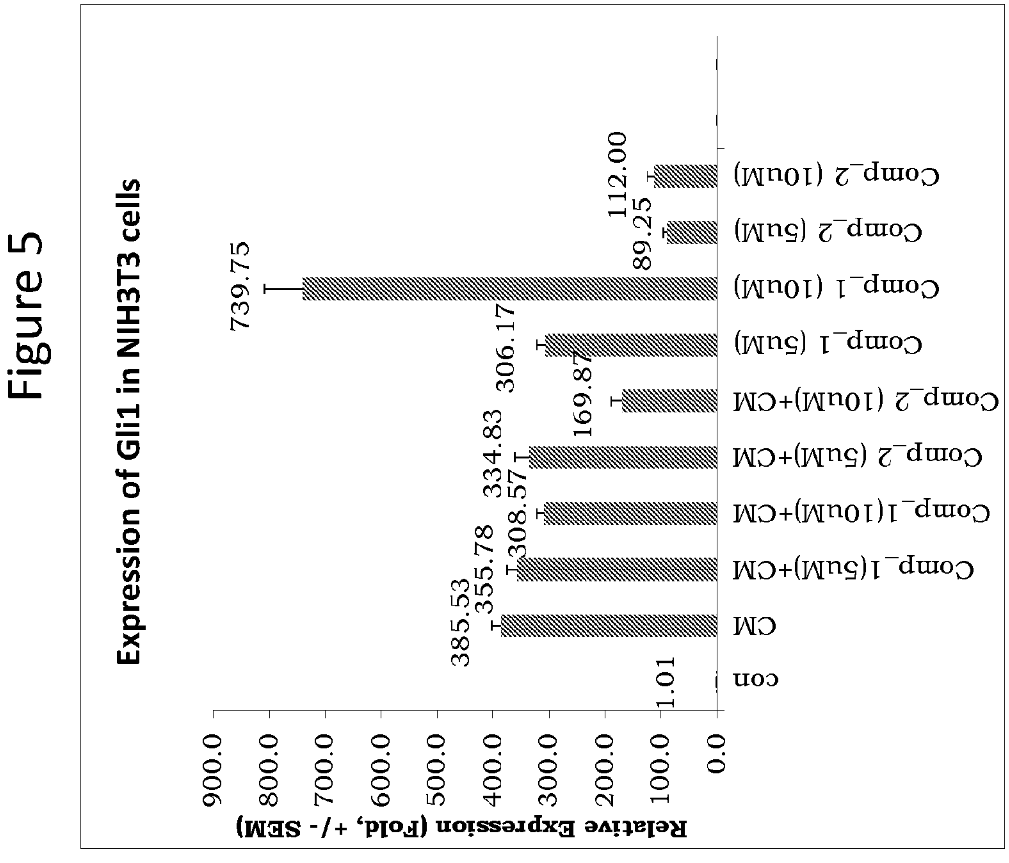

Compound 1

Compound 5

Compound 10

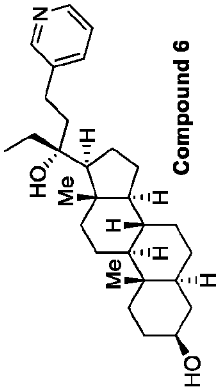
Compound 6
Figure 7
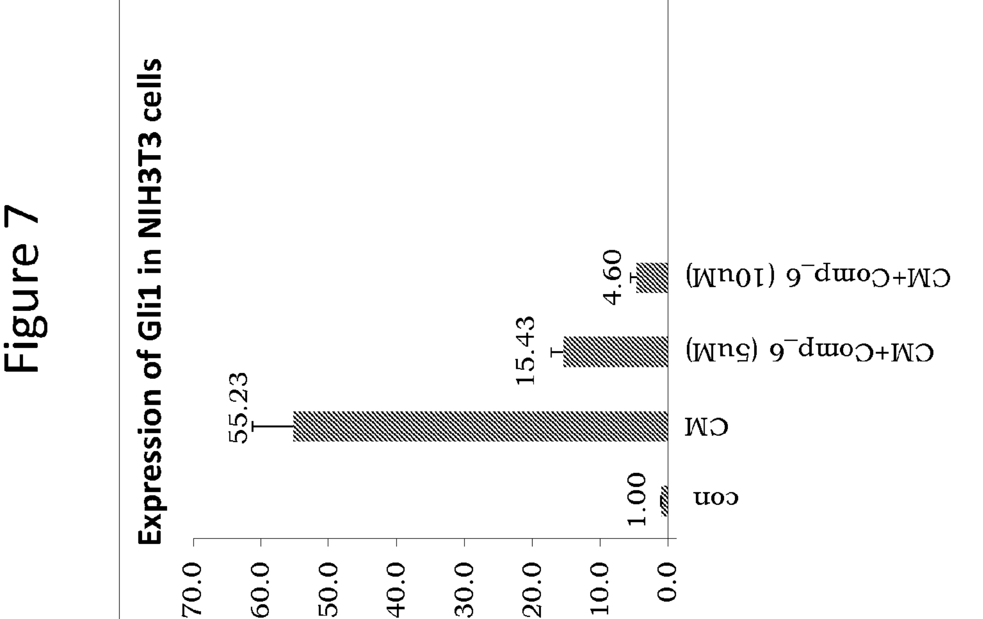

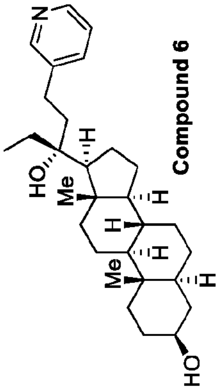
Compound 6
Figure 8
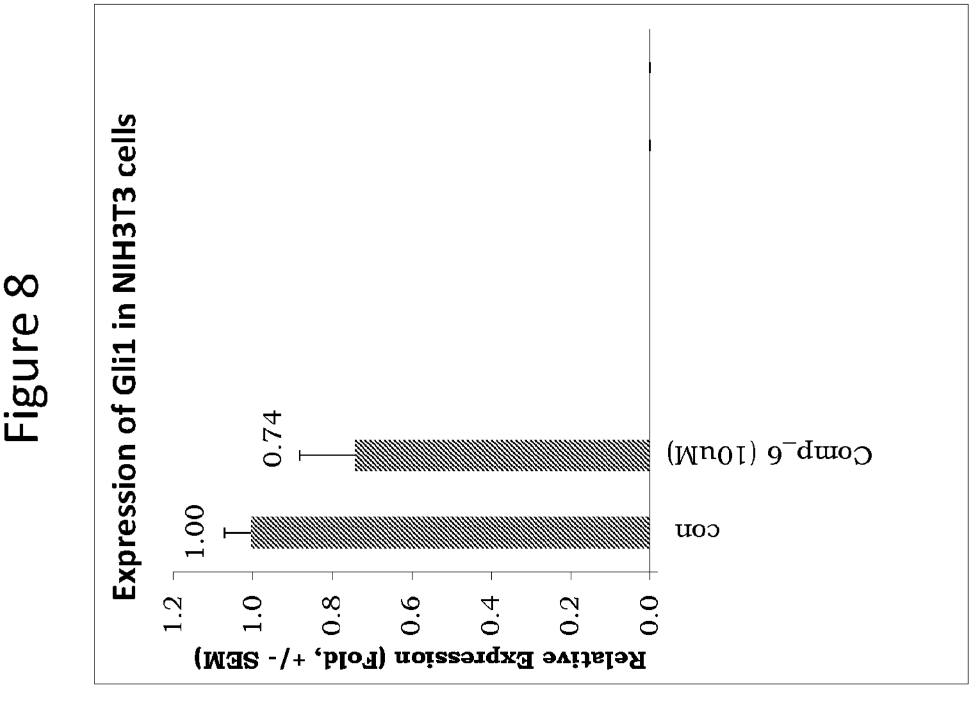

Compound 17

OXYSTEROL COMPOUNDS AND USES THEREOF

CROSS-REFERENCE

This application is a § 371 U.S. national stage entry of International Application No. PCT/US21/35973, filed Jun. 4, 2021, which claims benefit of U.S. Provisional Patent Application No. 63/035,597, filed on Jun. 5, 2020, each of which is incorporated herein by reference in its entirety.

BACKGROUND OF THE INVENTION

Hedgehog (Hh) pathway plays a key role in embryogenesis, development, and tissue maintenance.

SUMMARY OF THE INVENTION

Described herein are inhibitors and activators of Hedgehog signaling. Also disclosed herein are methods for synthesizing such Hedgehog signaling inhibitors. Further described are pharmaceutical formulations that include a Hedgehog signaling inhibitor.

In one aspect is a compound of Formula (I), or a pharmaceutically acceptable salt or solvate thereof:

Formula (I)

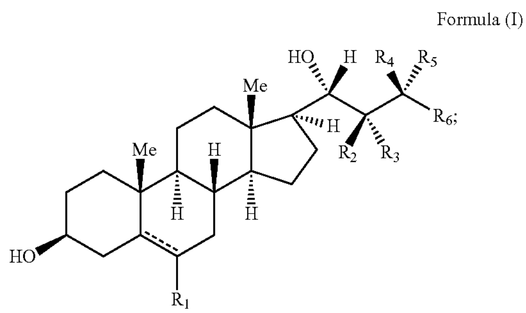

wherein:

- ------ is a single or double bond;
- $R_1$ is hydrogen or —OH;
- $R_2$, $R_3$, $R_4$, and $R_5$ are independently hydrogen, deuterium, $C_1$-$C_8$alkyl, or —OH;
- $R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;
- each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$;
- each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;
- each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl, and

- each $R_{11}$ is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

In some embodiments are compounds of Formula (I) having the structure of Formula (Ia):

Formula (Ia)

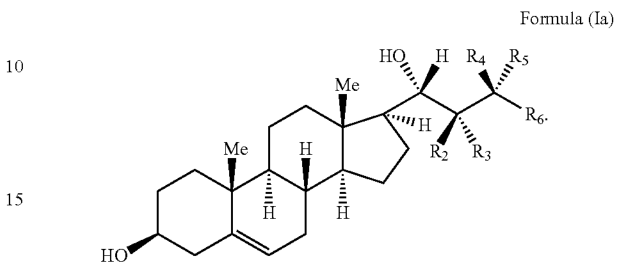

In some embodiments are compounds of Formula (I) having the structure of Formula (Ib):

Formula (Ib)

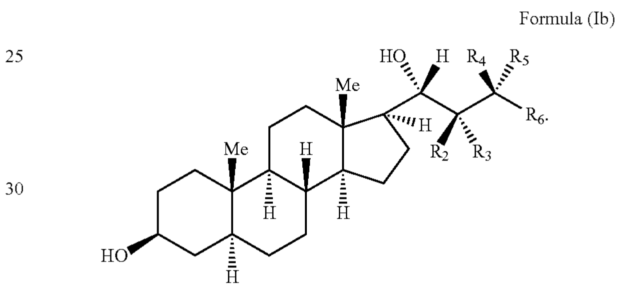

In some embodiments are compounds of Formula (I) having the structure of Formula (Ic):

Formula (Ic)

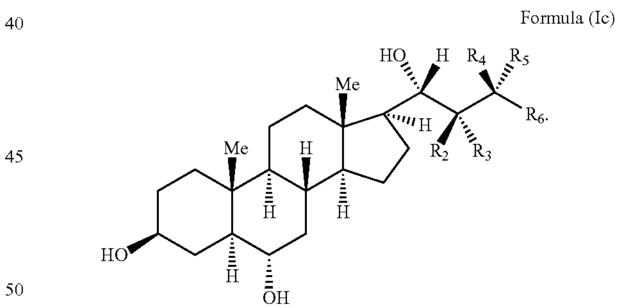

In some embodiments is a compound of Formula (I), (Ia), (Ib), or (Ic), wherein $R_2$, $R_3$, $R_4$, and $R_5$ are each hydrogen. In some embodiments is a compound of Formula (I), (Ia), (Ib), or (Ic), wherein $R_2$, $R_3$, $R_4$, and $R_5$ are each deuterium. In some embodiments is a compound of Formula (I), (Ia), (Ib), or (Ic), wherein $R_6$ is $C_6$-$C_{10}$aryl optionally substituted with 1, 2, 3, or 4 $R_7$ groups. In some embodiments is a compound of Formula (I), (Ia), (Ib), or (Ic), wherein $R_6$ is phenyl substituted with 1, 2, or 3 $R_7$ groups. In some embodiments is a compound of Formula (I), (Ia), (Ib), or (Ic), wherein each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), (Ia), (Ib), or (Ic), wherein $R_6$ is phenyl substituted with 1 $R_7$ group and $R_7$ is halogen. In some embodiments is a compound of Formula (I), (Ia), (Ib), or (Ic), wherein $R_6$ is phenyl substituted with 1 $R_7$ group and $R_7$ is fluoro. In some embodiments is a compound of Formula (I), (Ia), (Ib), or (Ic), wherein $R_6$ is phenyl substituted with 1 $R_7$ group and $R_7$ is unsubstituted phenyl. In some embodiments is a compound of Formula (I), (Ia), (Ib), or (Ic), wherein $R_6$ is unsubstituted phenyl. In some embodiments is a compound of Formula (I), (Ia), (Ib), or (Ic), wherein $R_6$ is $C_2$-$C_9$heteroaryl optionally substituted with 1, 2, or 3 $R_7$ groups. In some embodiments is a compound of Formula (I), (Ia), (Ib), or (Ic), wherein $R_6$ is pyridyl optionally substituted with 1 or 2 $R_7$ groups. In some embodiments is a compound of Formula (I), (Ia), (Ib), or (Ic), wherein each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), (Ia), (Ib), or (Ic), wherein $R_6$ is unsubstituted pyridyl.

In another aspect, provided herein, is a pharmaceutical composition comprising a compound of Formula (I), (Ia), (Ib), or (Ic), and a pharmaceutically acceptable excipient.

Also provided herein, in some embodiments, is a method of modulating Hedgehog signaling in a mammal, comprising administering to the mammal a compound of Formula (I), (Ia), (Ib), or (Ic). In some embodiments, is a method of modulating Hedgehog signaling in a mammal, comprising administering to the mammal a compound of Formula (I), (Ia), (Ib), or (Ic), wherein Hedgehog signaling is positively modulated. In some embodiments, is a method of modulating Hedgehog signaling in a mammal, comprising administering to the mammal a compound of Formula (I), (Ia), (Ib), or (Ic), wherein Hedgehog signaling is negatively modulated.

BRIEF DESCRIPTION OF THE FIGURE

FIG. 5 shows the relative expression of Hedgehog target gene Gli1 in NIH3T3 cells treated with Compound 1 or Compound 2. The relative expression (fold) of Gli1 is plotted for Compound 1 and Compound 2, each at concentrations of 5 μM and 10 μM in conditioned medium (CM) or 5% FBS in DMEM in comparison with a control (DMSO alone) and CM.

FIG. 7 shows the relative expression of Hedgehog target gene Gli1 in NIH3T3 cells treated with Compound 6 in conditioned medium (CM). The relative expression (fold) of Gli1 is plotted for Compound 6 at concentrations of 5 μM and 10 μM in conditioned medium (CM) in comparison with a CM.

FIG. 8 shows the relative expression of Hedgehog target gene Gli1 in NIH3T3 cells treated with Compound 6. The relative expression (fold) of Gli1 is plotted for Compound 6 at concentration of 10 μM in 5% FBS in DMEM in comparison with a control (DMSO alone).

DETAILED DESCRIPTION OF THE INVENTION

Hedgehog Signaling

The Hedgehog signaling pathway is a cell signalling pathway that is activated by a Hedgehog ligand (Sonic hedgehog (SHh), Desert hedgehog (DHh), and Indian hedgehog (IHh)). The pathway is one of the key regulators of embryonic development, but Hedgehog signaling remains important in the adult. Sonic hedgehog has been shown to promote the proliferation of adult stem cells from various tissues. The initiating step in Hedgehog signaling is controlled by an interaction between two transmembrane proteins, Patched 1 (PTCH) and Smoothened (Smo). Upon binding of a Hedgehog agonist, PTCH is inactivated and Smo is released allowing Gli transcription factors to initiate target gene transcription. Smo can function as an oncogene. Activating Smo mutations can lead to unregulated activation of the Hedgehog pathway.

Oxysterols can be activators or inhibitors of Hh signaling. For example, 20(S)-hydroxycholesterol (20(S)—OHC) (Compound 8) induces allosteric activation of Hh signaling in mesenchymal cells, while a related oxysterol, 20α,22(R)-dihydroxycholesterol (Compound 9), blocks Hh signaling. In subsequent studies, we were able to identify potent semisynthetic oxysterol derivatives, either as activators or inhibitors of Hh signaling, such as Hh activator (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol (Compound 10) and Hh inhibitors (3S,5S,8R,9S,10S,13S,14S,17S)-17-((R)-4-(4-fluorophenyl)-2-hydroxybutan-2-yl)-10,13-dimethylhexadecahydro-1H-cyclopenta[a]phenanthren-3-ol (Compound 11) and (3S,8S,9S,10R,13S,14S,17S)-17-((R)-2-hydroxy-4-(pyridin-3-yl)butan-2-yl)-10,13-dimethyl-2,3,4,7,8,9,10,11,12,13,14,15,16,17-tetradecahydro-1H-cyclopenta[a]phenanthren-3-ol (Compound 12), which also blocks TGFβ signaling.

(Compound 1)

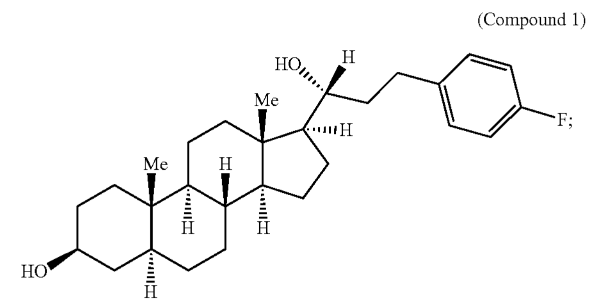
;

-continued
(Compound 2)
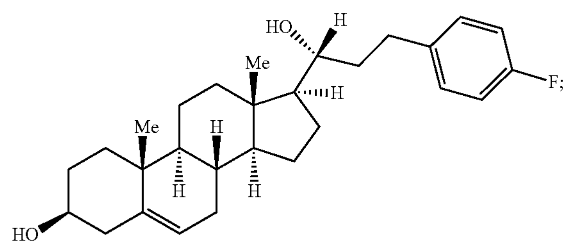
(Compound 3)
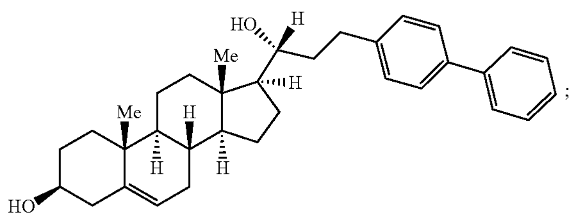
(Compound 4a)
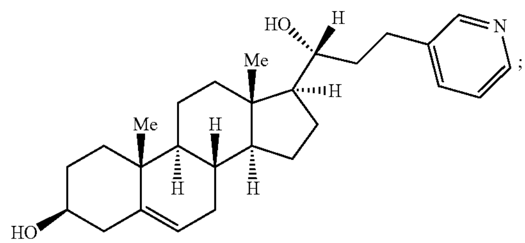
(Compound 4b)
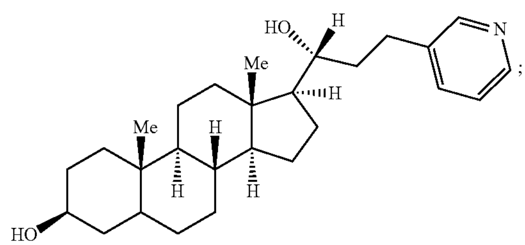
(Compound 5)
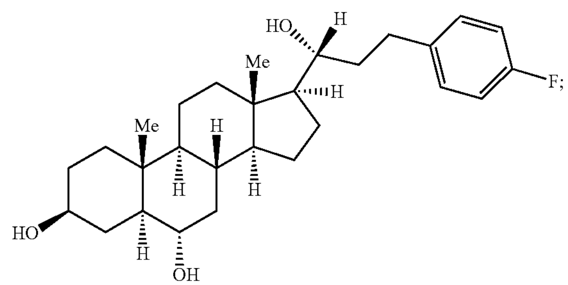
(Compound 6)
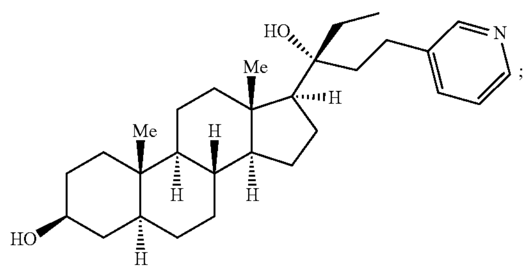
-continued
(Compound 7)
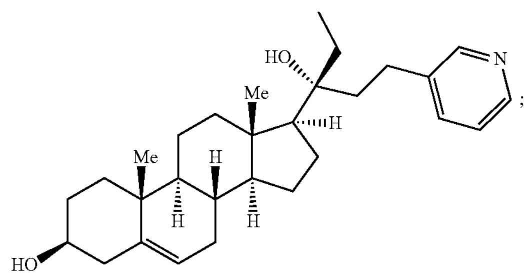
(Compound 8)
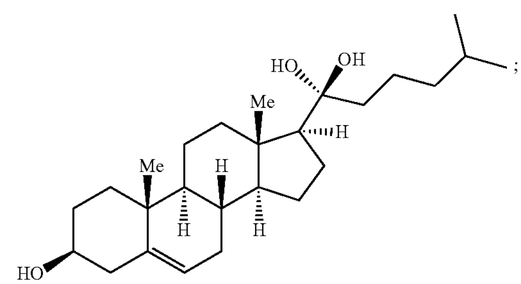
(Compound 9)
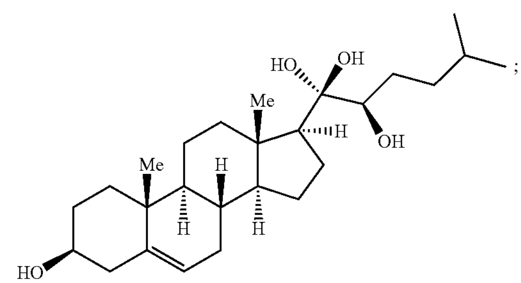
(Compound 10)
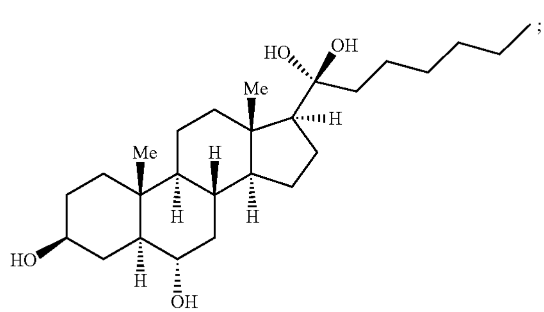
(Compound 11)
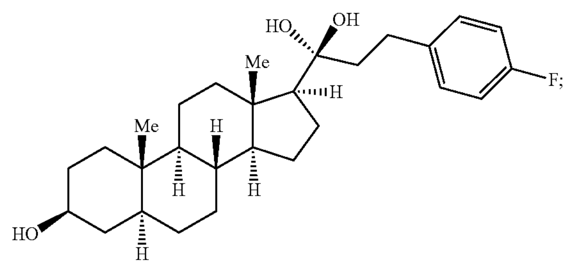

-continued (Compound 12)

(Compound 13)

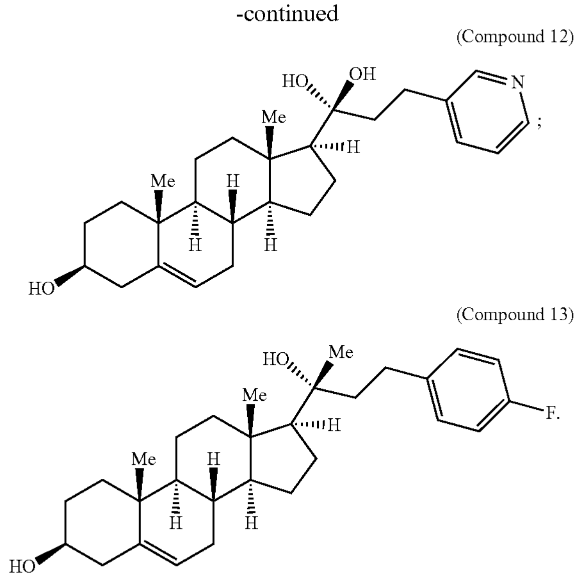

Figure 1:
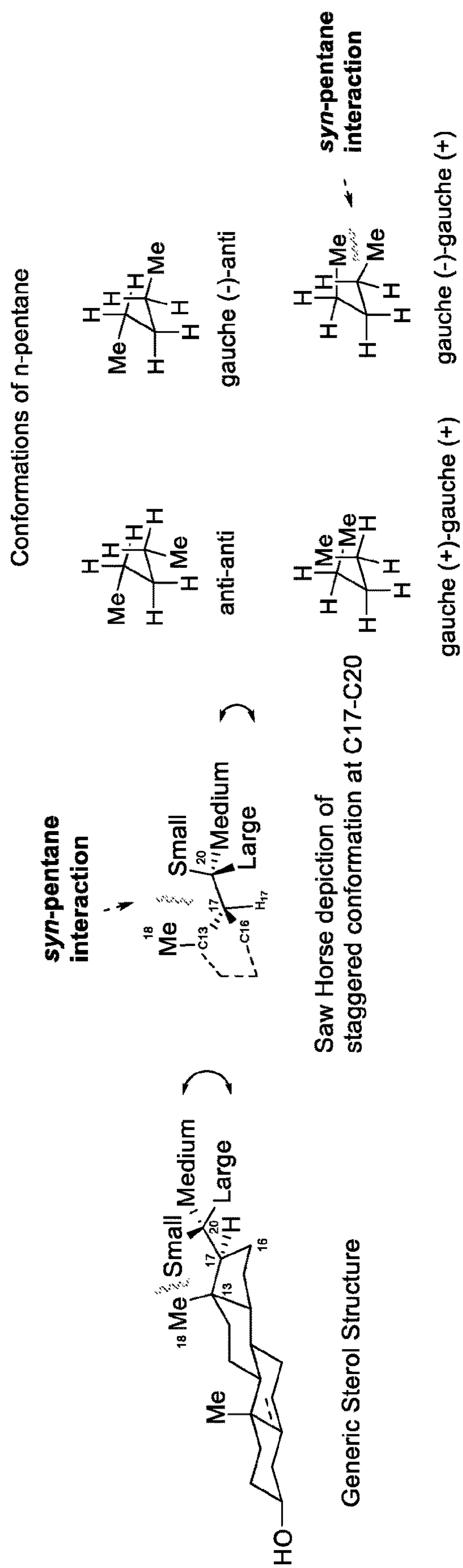
FIG. 1 illustrates a model for predicting conformational properties of oxysterols.
Figure 2:
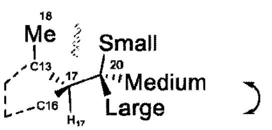
FIG. 2 illustrates conformational properties of Compound 5, Compound 10, and Compound 13.
Figure 2:
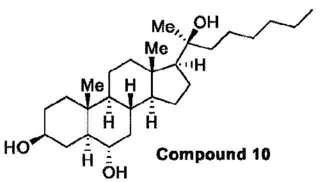
Figure 2:
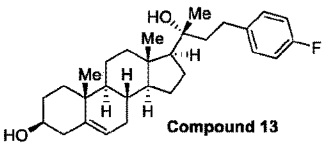
Figure 2:
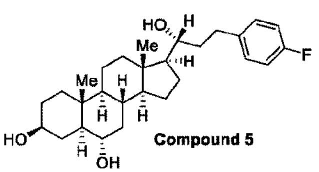
Figure 2:
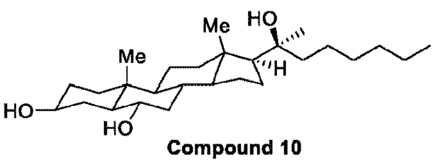
Figure 2:
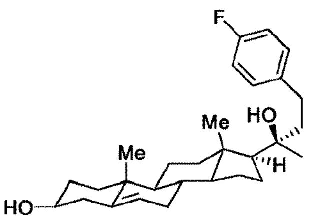
Figure 2:
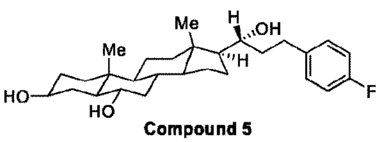
Figure 2:
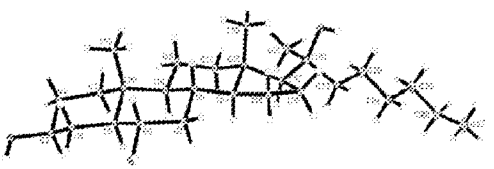
Figure 2:
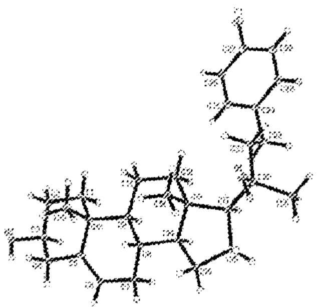
Figure 2:
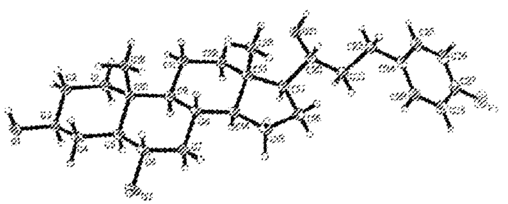

The biological properties of oxysterols depend in significant part on their molecular shape and conformational properties. The sterol side chain is conformationally the most flexible part of the otherwise rigid sterol molecules; however, the high degree of substitution across C-17, C-18 and C-20 significantly reduces the conformational flexibility in many sterols due to steric crowding, as illustrated in FIG. 1. This crowded substitution pattern can result in a preference for either an extended or bent conformation of the 'Large' substituent, usually the sterol side chain, depending on the stereochemical configuration of the C17-C20 bond. The 'Small' group at C-20 will align itself with the C-18 methyl group to minimize torsional strain of an unavoidable syn-pentane interaction. Therefore, the orientation of the side chain in sterols and oxysterols is predicted based on the substitution pattern and absolute configuration at C-20. For example, tertiary alcohols in the C20 (S)-configuration, such as Compound 8 and Compound 10, prefer the extended conformation, according to this model which was confirmed by x-ray crystallography (FIG. 2). By contrast, tertiary alcohols in the C20 (R)-configuration, such as Compound 11, Compound 12, and Compound 13, prefer a bent conformations of the sterol side chain, which was confirmed by X-ray crystallography (FIG. 2).

Figure 3:
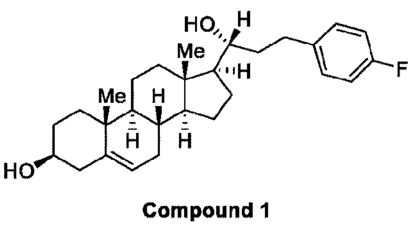
FIG. 3 depicts structures of Compound 1, Compound 2, Compound 3, Compound 4a, Compound 4b, Compound 5, Compound 6, and Compound 7.
Figure 3:
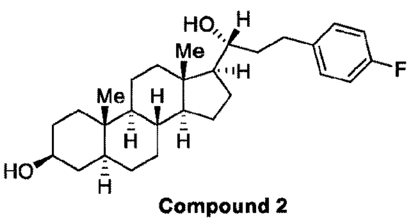
Figure 3:
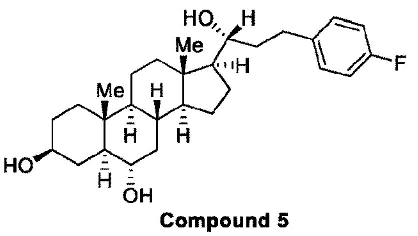
Figure 3:
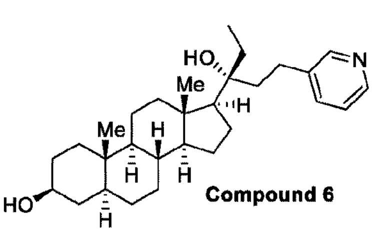
Figure 3:
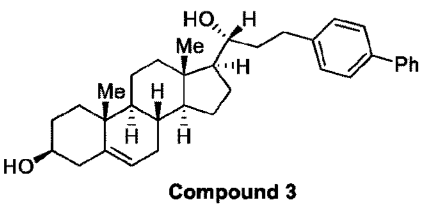
Figure 3:
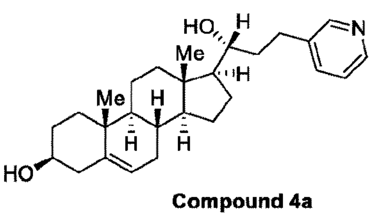
Figure 3:
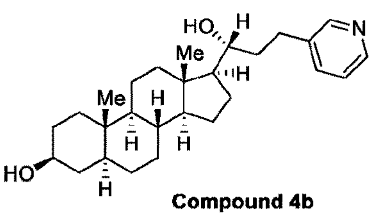
Figure 3:
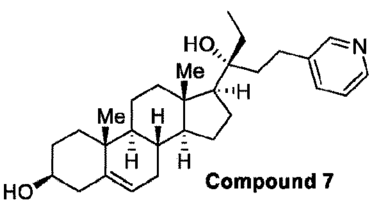
Figure 4:
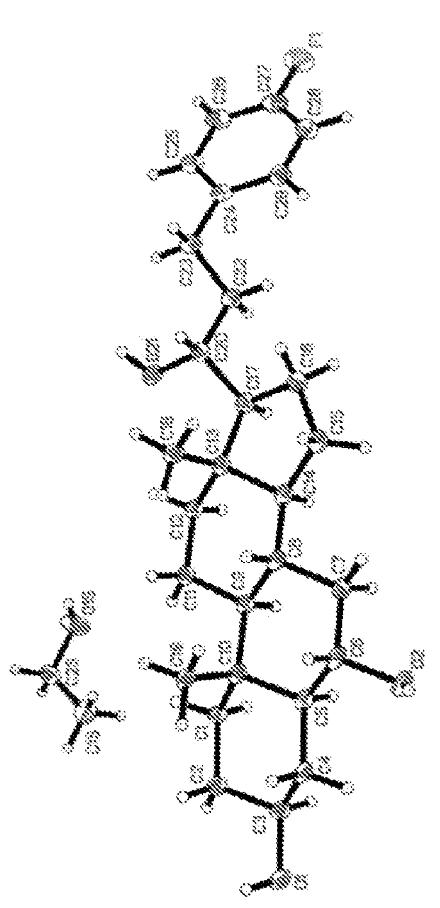
FIG. 4 illustrates an atomic displacement ellipsoid drawing of crystalline (3S,5S,6S,8S,9S,10R,13S,14S,17S)-17-((R)-3-(4-fluorophenyl)-1-hydroxypropyl)-10,13-dimethylhexadecahydro-1H-cyclopenta[a]phenanthrene-3,6-diol (Compound 5).

This pattern is reversed for C-20 secondary alcohols: for the C20 (S)-configuration, the sterol side chain is predicted to be bent, whereas for the C20 (R)-configuration, the sterol side chain is predicted to be extended. This model predicts that Compound 1, Compound 2, Compound 3, Compound 4a, Compound 4b, Compound 5, Compound 6, and Compound 7 shown in FIG. 3, prefer the extended conformation of the sterol side chain, which was confirmed by X-ray crystallography of Compound 5 (FIG. 4). Similarly, according to the model, cholesterol, a sterol in the C20 (R)-configuration, should prefer an extended conformation of the sterol side chain in which C-20 carbon hydrogen bond ('Small' group) is aligned with the C-18 methyl group. Indeed, this conformational preference of cholesterol has been confirmed in multiple crystallographic studies.

Definitions

As used herein, the terms "treat," "treating" or "treatment," include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment. In another embodiment, treatment refers to therapeutic treatment.

As used herein, "administer" means to provide a treatment, for example to prescribe a treatment, apply a treatment, or distribute a treatment. In some instances, to administer means a medical professional prescribes a treatment which a patient applies (e.g., the patient applies a CPAP device, consumes a medication, or injects a medication). Administration of a medical treatment does not require the immediate or constant supervision of a medical professional.

"Co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "subject" or "patient" encompasses mammals and non-mammals. "Mammals" include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

A "tissue" comprises two or more cells. The two or more cells may have a similar function and/or function. The tissue may be a connective tissue, epithelial tissue, muscular tissue, or nervous tissue. Alternatively, the tissue is a bone, tendon (both referred to as musculoskeletal grafts), cornea, skin, heart valve, or vein.

An "organ" comprises two or more tissues. The two or more tissues may perform a specific function or group of functions. In some instances, the organ is a lung, mouth, nose, parathyroid gland, pineal gland, pituitary gland, carotid body, salivary gland, skin, gall bladder, pancreas, small intestine, stomach, spleen, spinal cord, thymus, thyroid gland, trachea, uterus, or vermiform appendix. Alternatively, the organ is an adrenal gland, appendix, brain, bladder, kidney, intestine, large intestine, small intestine, liver, heart, or muscle.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, amido. In one embodiment, the referenced group is substituted with one or more halogen. In another embodiment, the referenced group is substituted with one or more alkyl.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NR$_2$ or —NRC(O)R, where each R is independently selected from hydrogen, alkyl, cycloalkyl, aryl, heteroaryl and heterocycloalkyl.

The term "ester" refers to a chemical moiety with formula —C(═O)OR, where R is selected from the group consisting of alkyl, cycloalkyl, aryl, heteroaryl and heterocycloalkyl.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to tetrahydronaphthyl, indanyl, tetrahydropentalene or the like. Polycyclic cycloalkyls include adamantane, norbornane or the like. The term cycloalkyl includes "unsaturated nonaromatic carbocyclyl" or "nonaromatic unsaturated carbocyclyl" groups both of which refer to a nonaromatic carbocycle, as defined herein, that contains at least one carbon carbon double bond or one carbon carbon triple bond.

The term "heterocyclo" refers to heteroaromatic and heterocycloalkyl groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Examples of monocyclic heteroaryl groups include and are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heteroalicyclic" group or "heterocycloalkyl" group or "heterocyclyl" group refers to a cycloalkyl group, wherein at least one skeletal ring atom is a heteroatom selected from nitrogen, oxygen and sulfur. In various embodiments, heterocycloalkyls are saturated, or partially unsaturated. In some embodiments, the radicals are fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, $—CH_2—O—CH_3$, $—CH_2—CH_2—O—CH_3$, $—CH_2—NH—CH_3$, $—CH_2—CH_2—NH—CH_3$, $—CH_2—N(CH_3)—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH{=}CH—N(CH_3)—CH_3$. In some embodiments, up to two heteroatoms are consecutive, such as, by way of example, $—CH_2—NH—OCH_3$ and $—CH_2—O—Si(CH_3)_3$.

A "cyano" group refers to a CN group.

An "isocyanato" group refers to a NCO group.

A "thiocyanato" group refers to a CNS group.

An "isothiocyanato" group refers to a NCS group.

"Alkoyloxy" refers to a RC(=O)O— group.

"Alkoyl" refers to a RC(=O)— group.

Compounds

Described herein are compounds of Formula (I), (Ia), (Ib), or (Ic) which are modulators of Hedgehog signaling. Also described herein are pharmaceutically acceptable salts, and pharmaceutically acceptable solvates of such compounds. Pharmaceutical compositions that include at least one such compound or a pharmaceutically acceptable salt or solvate of such compound, are provided. In certain embodiments, isomers and chemically protected forms of compounds having a structure represented by any of Formula (I), (Ia), (Ib), or (Ic) are also provided.

In some embodiments is a compound having the structure of Formula (I):

Formula (I)

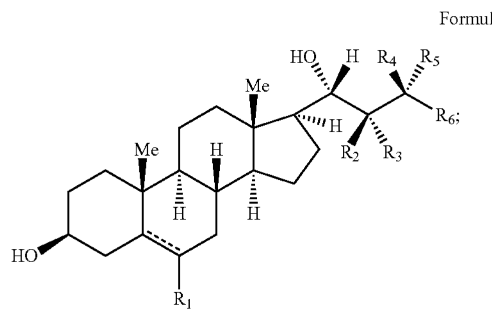

wherein:

------ is a single or double bond;

$R_1$ is hydrogen or —OH;

$R_2$, $R_3$, $R_4$, and $R_5$ are independently hydrogen, deuterium, $C_1$-$C_8$alkyl, or —OH;

$R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;

each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, $—OR_8$, $—SR_8$, $—N(R_9)(R_{10})$, $—C(O)OR_9$, $—C(O)N(R_9)(R_{10})$, $—C(O)R_{11}$, $—S(O)_2R_{11}$, and $—S(O)_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, $—OR_8$, $—SR_8$, $—N(R_9)(R_{10})$, $—C(O)OR_9$, $—C(O)N(R_9)(R_{10})$, $—C(O)R_{11}$, $—S(O)_2R_{11}$, and $—S(O)_2N(R_9)(R_{10})$;

each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;

each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl; and each $R_{11}$ is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

In some embodiments is a compound of Formula (I) wherein ------ is a single bond. In some embodiments is a compound of Formula (I) wherein ------ is a double bond.

In some embodiments is a compound of Formula (I), wherein $R_1$ is hydrogen. In some embodiments is a compound of Formula (I), wherein $R_1$ is —OH.

In some embodiments is a compound of Formula (I), wherein $R_6$ is $C_6$-$C_{10}$aryl optionally substituted with 1, 2, 3, or 4 $R_7$ groups. In some embodiments is a compound of Formula (I), wherein $R_6$ is $C_6$-$C_{10}$aryl substituted with 1, 2, or 3 $R_7$ groups. In some embodiments is a compound of Formula (I), wherein $R_6$ is phenyl substituted with 1, 2, or 3 $R_7$ groups. In some embodiments is a compound of Formula (I), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1 $R_7$ group and $R_7$ is halogen. In some embodiments is a compound of Formula (I), wherein $R_6$ is phenyl substituted with 1 $R_7$ group and $R_7$ is fluoro. In some embodiments is a compound of Formula (I), wherein $R_6$ is phenyl substituted with 1 $R_7$ group and $R_7$ is $C_{1-6}$alkyl optionally substituted with one, two, or three groups independently selected from halogen. In some embodiments is a compound of Formula (I), wherein $R_6$ is phenyl substituted with 1 $R_7$ group and $R_7$ is unsubstituted $C_{1-6}$alkyl. In some embodiments is a compound of Formula (I), wherein $R_6$ is phenyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is phenyl substituted with 1 $R_7$ group and $R_7$ is unsubstituted phenyl.

In some embodiments is a compound of Formula (I), wherein $R_6$ is unsubstituted phenyl.

In some embodiments is a compound of Formula (I), wherein $R_6$ is $C_2$-$C_9$heteroaryl optionally substituted with 1, 2, or 3 $R_7$ groups. In some embodiments is a compound of Formula (I), wherein $R_6$ is phenyl substituted with 1, 2, or 3 $R_7$ groups. In some embodiments is a compound of Formula (I), wherein $R_6$ is $C_2$-$C_9$heteroaryl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 $R_7$ group and $R_7$ is halogen. In some embodiments is a compound of Formula (I), wherein $R_6$ is $C_2$-$C_9$heteroaryl substituted with 1 $R_7$ group and $R_7$ is fluoro. In some embodiments is a compound of Formula (I), wherein $R_6$ is $C_2$-$C_9$heteroaryl substituted with 1 $R_7$ group and $R_7$ is $C_{1-6}$alkyl optionally substituted with one, two, or three groups independently selected from halogen. In some embodiments is a compound of Formula (I), wherein $R_6$ is $C_2$-$C_9$heteroaryl substituted with 1 $R_7$ group and $R_7$ is unsubstituted $C_{1-6}$alkyl. In some embodiments is a compound of Formula (I), wherein $R_6$ is $C_2$-$C_9$heteroaryl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is $C_2$-$C_9$heteroaryl substituted with 1 $R_7$ group and $R_7$ is unsubstituted phenyl.

In some embodiments is a compound of Formula (I), wherein $R_6$ is unsubstituted $C_2$-$C_9$heteroaryl.

In some embodiments is a compound of Formula (I), wherein $R_6$ is pyridyl optionally substituted with 1, 2, or 3 $R_7$ groups. In some embodiments is a compound of Formula (I), wherein $R_6$ is phenyl substituted with 1, 2, or 3 $R_7$ groups. In some embodiments is a compound of Formula (I), wherein $R_6$ is pyridyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 $R_7$ group and $R_7$ is halogen. In some embodiments is a compound of Formula (I), wherein $R_6$ is pyridyl substituted with 1 $R_7$ group and $R_7$ is fluoro. In some embodiments is a compound of Formula (I), wherein $R_6$ is pyridyl substituted with 1 $R_7$ group and $R_7$ is $C_{1-6}$alkyl optionally substituted with one, two, or three groups independently selected from halogen. In some embodiments is a compound of Formula (I), wherein $R_6$ is pyridyl substituted with 1 $R_7$ group and $R_7$ is unsubstituted $C_{1-6}$alkyl. In some embodiments is a compound of Formula (I), wherein $R_6$ is pyridyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (I), wherein $R_6$ is pyridyl substituted with 1 $R_7$ group and $R_7$ is unsubstituted phenyl.

In some embodiments is a compound of Formula (I), wherein $R_6$ is unsubstituted pyridyl.

In some embodiments is a compound of Formula (I), wherein $R_2$, $R_3$, $R_4$, and $R_5$ are each hydrogen. In some embodiments is a compound of Formula (I), wherein $R_2$, $R_3$, $R_4$, and $R_5$ are each deuterium. In some embodiments is a compound of Formula (I), wherein $R_2$ is —OH, and $R_3$, $R_4$, and $R_5$ are each hydrogen. In some embodiments is a compound of Formula (I), wherein $R_3$ is —OH, and $R_2$, $R_4$, and $R_5$ are each hydrogen. In some embodiments is a compound of Formula (I), wherein $R_2$ and $R_4$ are each —OH, and $R_3$ and $R_5$ are each hydrogen. In some embodiments is a compound of Formula (I), wherein $R_2$ and $R_5$ are each —OH, and $R_3$ and $R_4$ are each hydrogen. In some embodiments is a compound of Formula (I), wherein $R_3$ and $R_4$ are each —OH, and $R_2$ and $R_5$ are each hydrogen. In some embodiments is a compound of Formula (I), wherein $R_3$ and $R_5$ are each —OH, and $R_2$ and $R_4$ are each hydrogen.

In some embodiments is a compound having the structure of Formula (Ia):

Formula (Ia)

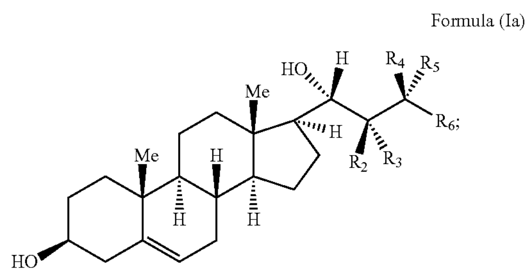

wherein:

- $R_2$, $R_3$, $R_4$, and $R_5$ are independently hydrogen, deuterium, $C_1$-$C_8$alkyl, or —OH;
- $R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;
- each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$;
- each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;
- each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl; and
- each $R_{11}$ is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

In some embodiments is a compound of Formula (Ia), wherein $R_6$ is $C_6$-$C_{10}$aryl optionally substituted with 1, 2, 3, or 4 $R_7$ groups. In some embodiments is a compound of Formula (Ia), wherein $R_6$ is $C_6$-$C_{10}$aryl substituted with 1, 2, or 3 $R_7$ groups. In some embodiments is a compound of Formula (Ia), wherein $R_6$ is phenyl substituted with 1, 2, or 3 $R_7$ groups. In some embodiments is a compound of Formula (Ia), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1 $R_7$ group and $R_7$ is halogen. In some embodiments is a compound of Formula (Ia), wherein $R_6$ is phenyl substituted with 1 $R_7$ group and $R_7$ is fluoro. In some embodiments is a compound of Formula (Ia), wherein $R_6$ is phenyl substituted with 1 $R_7$ group and $R_7$ is $C_{1-6}$alkyl optionally substituted with one, two, or three groups independently selected from halogen. In some embodiments is a compound of Formula (Ia), wherein $R_6$ is phenyl substituted with 1 $R_7$ group and $R_7$ is unsubstituted $C_{1-6}$alkyl. In some embodiments is a compound of Formula (Ia), wherein $R_6$ is phenyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is phenyl substituted with 1 $R_7$ group and $R_7$ is unsubstituted phenyl.

In some embodiments is a compound of Formula (Ia), wherein $R_6$ is unsubstituted phenyl.

In some embodiments is a compound of Formula (Ia), wherein $R_6$ is $C_2$-$C_9$heteroaryl optionally substituted with 1, 2, or 3 $R_7$ groups. In some embodiments is a compound of Formula (Ia), wherein $R_6$ is phenyl substituted with 1, 2, or 3 $R_7$ groups. In some embodiments is a compound of Formula (Ia), wherein $R_6$ is $C_2$-$C_9$heteroaryl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 $R_7$ group and $R_7$ is halogen. In some embodiments is a compound of Formula (Ia), wherein $R_6$ is $C_2$-$C_9$heteroaryl substituted with 1 $R_7$ group and $R_7$ is fluoro. In some embodiments is a compound of Formula (Ia), wherein $R_6$ is $C_2$-$C_9$heteroaryl substituted with 1 $R_7$ group and $R_7$ is $C_{1-6}$alkyl optionally substituted with one, two, or three groups independently selected from halogen. In some embodiments is a compound of Formula (Ia), wherein $R_6$ is $C_2$-$C_9$heteroaryl substituted with 1 $R_7$ group and $R_7$ is unsubstituted $C_{1-6}$alkyl. In some embodiments is a compound of Formula (Ia), wherein $R_6$ is $C_2$-$C_9$heteroaryl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is $C_2$-$C_9$heteroaryl substituted with 1 $R_7$ group and $R_7$ is unsubstituted phenyl.

In some embodiments is a compound of Formula (Ia), wherein $R_6$ is unsubstituted $C_2$-$C_9$heteroaryl.

In some embodiments is a compound of Formula (Ia), wherein $R_6$ is pyridyl optionally substituted with 1, 2, or 3 $R_7$ groups. In some embodiments is a compound of Formula (Ia), wherein $R_6$ is phenyl substituted with 1, 2, or 3 $R_7$ groups. In some embodiments is a compound of Formula (Ia), wherein $R_6$ is pyridyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 $R_7$ group and $R_7$ is halogen. In some embodiments is a compound of Formula (Ia), wherein $R_6$ is pyridyl substituted with 1 $R_7$ group and $R_7$ is fluoro. In some embodiments is a compound of Formula (Ia), wherein $R_6$ is pyridyl substituted with 1 $R_7$ group and $R_7$ is $C_{1-6}$alkyl optionally substituted with one, two, or three groups independently selected from halogen. In some embodiments is a compound of Formula (Ia), wherein $R_6$ is pyridyl substituted with 1 $R_7$ group and $R_7$ is unsubstituted $C_{1-6}$alkyl. In some embodiments is a compound of Formula (Ia), wherein $R_6$ is pyridyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ia), wherein $R_6$ is pyridyl substituted with 1 $R_7$ group and $R_7$ is unsubstituted phenyl.

In some embodiments is a compound of Formula (Ia), wherein $R_6$ is unsubstituted pyridyl.

In some embodiments is a compound of Formula (Ia), wherein $R_2$, $R_3$, $R_4$, and $R_5$ are each hydrogen. In some embodiments is a compound of Formula (Ia), wherein $R_2$, $R_3$, $R_4$, and $R_5$ are each deuterium. In some embodiments is a compound of Formula (Ia), wherein $R_2$ is —OH, and $R_3$, $R_4$, and $R_5$ are each hydrogen. In some embodiments is a compound of Formula (Ia), wherein $R_3$ is —OH, and $R_2$, $R_4$, and $R_5$ are each hydrogen. In some embodiments is a compound of Formula (Ia), wherein $R_2$ and $R_4$ are each —OH, and $R_3$ and $R_5$ are each hydrogen. In some embodiments is a compound of Formula (Ia), wherein $R_2$ and $R_5$ are each —OH, and $R_3$ and $R_4$ are each hydrogen. In some embodiments is a compound of Formula (Ia), wherein $R_3$ and $R_4$ are each —OH, and $R_2$ and $R_5$ are each hydrogen. In some embodiments is a compound of Formula (Ia), wherein $R_3$ and $R_5$ are each —OH, and $R_2$ and $R_4$ are each hydrogen.

In some embodiments is a compound having the structure of Formula (Ib):

Formula (Ib)

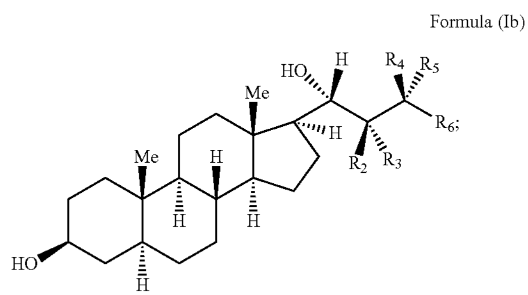

wherein:

- $R_2$, $R_3$, $R_4$, and $R_5$ are independently hydrogen, deuterium, $C_1$-$C_8$alkyl, or —OH;
- $R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;
- each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$;
- each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;
- each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl; and
- each Ru is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

In some embodiments is a compound of Formula (Ib), wherein $R_6$ is $C_6$-$C_{10}$aryl optionally substituted with 1, 2, 3, or 4 $R_7$ groups. In some embodiments is a compound of Formula (Ib), wherein $R_6$ is $C_6$-$C_{10}$aryl substituted with 1, 2, or 3 $R_7$ groups. In some embodiments is a compound of Formula (Ib), wherein $R_6$ is phenyl substituted with 1, 2, or 3 $R_7$ groups. In some embodiments is a compound of Formula (Ib), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1 $R_7$ group and $R_7$ is halogen. In some embodiments is a compound of Formula (Ib), wherein $R_6$ is phenyl substituted with 1 $R_7$ group and $R_7$ is fluoro. In some embodiments is a compound of Formula (Ib), wherein $R_6$ is phenyl substituted with 1 $R_7$ group and $R_7$ is $C_{1-6}$alkyl optionally substituted with one, two, or three groups independently selected from halogen. In some embodiments is a compound of Formula (Ib), wherein $R_6$ is phenyl substituted with 1 $R_7$ group and $R_7$ is unsubstituted $C_{1-6}$alkyl. In some embodiments is a compound of Formula (Ib), wherein $R_6$ is phenyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is phenyl substituted with 1 $R_7$ group and $R_7$ is unsubstituted phenyl.

In some embodiments is a compound of Formula (Ib), wherein $R_6$ is unsubstituted phenyl.

In some embodiments is a compound of Formula (Ib), wherein $R_6$ is $C_2$-$C_9$heteroaryl optionally substituted with 1, 2, or 3 $R_7$ groups. In some embodiments is a compound of Formula (Ib), wherein $R_6$ is phenyl substituted with 1, 2, or 3 $R_7$ groups. In some embodiments is a compound of Formula (Ib), wherein $R_6$ is $C_2$-$C_9$heteroaryl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 $R_7$ group and $R_7$ is halogen. In some embodiments is a compound of Formula (Ib), wherein $R_6$ is $C_2$-$C_9$heteroaryl substituted with 1 $R_7$ group and $R_7$ is fluoro. In some embodiments is a compound of Formula (Ib), wherein $R_6$ is $C_2$-$C_9$heteroaryl substituted with 1 $R_7$ group and $R_7$ is $C_{1-6}$alkyl optionally substituted with one, two, or three groups independently selected from halogen. In some embodiments is a compound of Formula (Ib), wherein $R_6$ is $C_2$-$C_9$heteroaryl substituted with 1 $R_7$ group and $R_7$ is unsubstituted $C_{1-6}$alkyl. In some embodiments is a compound of Formula (Ib), wherein $R_6$ is $C_2$-$C_9$heteroaryl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is $C_2$-$C_9$heteroaryl substituted with 1 $R_7$ group and $R_7$ is unsubstituted phenyl.

In some embodiments is a compound of Formula (Ib), wherein $R_6$ is unsubstituted $C_2$-$C_9$heteroaryl.

In some embodiments is a compound of Formula (Ib), wherein $R_6$ is pyridyl optionally substituted with 1, 2, or 3 $R_7$ groups. In some embodiments is a compound of Formula (Ib), wherein $R_6$ is phenyl substituted with 1, 2, or 3 $R_7$ groups. In some embodiments is a compound of Formula (Ib), wherein $R_6$ is pyridyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 $R_7$ group and $R_7$ is halogen. In some embodiments is a compound of Formula (Ib), wherein $R_6$ is pyridyl substituted with 1 $R_7$ group and $R_7$ is fluoro. In some embodiments is a compound of Formula (Ib), wherein $R_6$ is pyridyl substituted with 1 $R_7$ group and $R_7$ is $C_{1-6}$alkyl optionally substituted with one, two, or three groups independently selected from halogen. In some embodiments is a compound of Formula (Ib), wherein $R_6$ is pyridyl substituted with 1 $R_7$ group and $R_7$ is unsubstituted $C_{1-6}$alkyl. In some embodiments is a compound of Formula (Ib), wherein $R_6$ is pyridyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ib), wherein $R_6$ is pyridyl substituted with 1 $R_7$ group and $R_7$ is unsubstituted phenyl.

In some embodiments is a compound of Formula (Ib), wherein $R_6$ is unsubstituted pyridyl.

In some embodiments is a compound of Formula (Ib), wherein $R_2$, $R_3$, $R_4$, and $R_5$ are each hydrogen. In some embodiments is a compound of Formula (Ib), wherein $R_2$, $R_3$, $R_4$, and $R_5$ are each deuterium. In some embodiments is a compound of Formula (Ib), wherein $R_2$ is —OH, and $R_3$, $R_4$, and $R_5$ are each hydrogen. In some embodiments is a compound of Formula (Ib), wherein $R_3$ is —OH, and $R_2$, $R_4$, and $R_5$ are each hydrogen. In some embodiments is a compound of Formula (Ib), wherein $R_2$ and $R_4$ are each —OH, and $R_3$ and $R_5$ are each hydrogen. In some embodiments is a compound of Formula (Ib), wherein $R_2$ and $R_5$ are each —OH, and $R_3$ and $R_4$ are each hydrogen. In some embodiments is a compound of Formula (Ib), wherein $R_3$ and $R_4$ are each —OH, and $R_2$ and $R_5$ are each hydrogen. In some embodiments is a compound of Formula (Ib), wherein $R_3$ and $R_5$ are each —OH, and $R_2$ and $R_4$ are each hydrogen.

In some embodiments is a compound having the structure of Formula (Ic):

Formula (Ic)

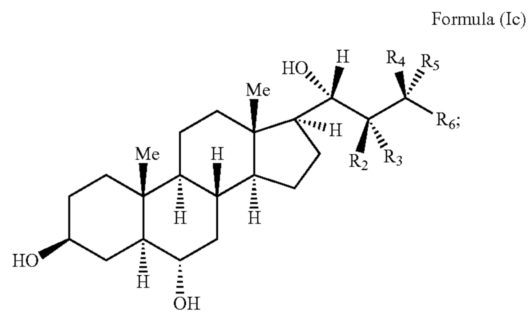

wherein:

- $R_2$, $R_3$, $R_4$, and $R_5$ are independently hydrogen, deuterium, $C_1$-$C_8$alkyl, or —OH;
- $R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;
- each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, —$OR_8$, —$SR_8$, —$N(R_9)(R_{10})$, —C(O)$OR_9$, —C(O)$N(R_9)(R_{10})$, —C(O)$R_{11}$, —S(O)$_2R_{11}$, and —S(O)$_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$alkoxy, $C_{1-6}$haloalkoxy, —$OR_8$, —$SR_8$, —$N(R_9)(R_{10})$, —C(O)$OR_9$, —C(O)$N(R_9)(R_{10})$, —C(O)$R_{11}$, —$S(O)_2R_{11}$, and —$S(O)_2N(R_9)(R_{10})$;

each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;

each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl; and each $R_{11}$ is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

In some embodiments is a compound of Formula (Ic), wherein $R_6$ is $C_6$-$C_{10}$aryl optionally substituted with 1, 2, 3, or 4 $R_7$ groups. In some embodiments is a compound of Formula (Ic), wherein $R_6$ is $C_6$-$C_{10}$aryl substituted with 1, 2, or 3 $R_7$ groups. In some embodiments is a compound of Formula (Ic), wherein $R_6$ is phenyl substituted with 1, 2, or 3 $R_7$ groups. In some embodiments is a compound of Formula (Ic), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1 $R_7$ group and $R_7$ is halogen. In some embodiments is a compound of Formula (Ic), wherein $R_6$ is phenyl substituted with 1 $R_7$ group and $R_7$ is fluoro. In some embodiments is a compound of Formula (Ic), wherein $R_6$ is phenyl substituted with 1 $R_7$ group and $R_7$ is $C_{1-6}$alkyl optionally substituted with one, two, or three groups independently selected from halogen. In some embodiments is a compound of Formula (Ic), wherein $R_6$ is phenyl substituted with 1 $R_7$ group and $R_7$ is unsubstituted $C_{1-6}$alkyl. In some embodiments is a compound of Formula (Ic), wherein $R_6$ is phenyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is phenyl substituted with 1 $R_7$ group and $R_7$ is unsubstituted phenyl.

In some embodiments is a compound of Formula (Ic), wherein $R_6$ is unsubstituted phenyl.

In some embodiments is a compound of Formula (Ic), wherein $R_6$ is $C_2$-$C_9$heteroaryl optionally substituted with 1, 2, or 3 $R_7$ groups. In some embodiments is a compound of Formula (Ic), wherein $R_6$ is phenyl substituted with 1, 2, or 3 $R_7$ groups. In some embodiments is a compound of Formula (Ic), wherein $R_6$ is $C_2$-$C_9$heteroaryl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 $R_7$ group and $R_7$ is halogen. In some embodiments is a compound of Formula (Ic), wherein $R_6$ is $C_2$-$C_9$heteroaryl substituted with 1 $R_7$ group and $R_7$ is fluoro. In some embodiments is a compound of Formula (Ic), wherein $R_6$ is $C_2$-$C_9$heteroaryl substituted with 1 $R_7$ group and $R_7$ is $C_{1-6}$alkyl optionally substituted with one, two, or three groups independently selected from halogen. In some embodiments is a compound of Formula (Ic), wherein $R_6$ is $C_2$-$C_9$heteroaryl substituted with 1 $R_7$ group and $R_7$ is unsubstituted $C_{1-6}$alkyl. In some embodiments is a compound of Formula (Ic), wherein $R_6$ is $C_2$-$C_9$heteroaryl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is $C_2$-$C_9$heteroaryl substituted with 1 $R_7$ group and $R_7$ is unsubstituted phenyl.

In some embodiments is a compound of Formula (Ic), wherein $R_6$ is unsubstituted $C_2$-$C_9$heteroaryl.

In some embodiments is a compound of Formula (Ic), wherein $R_6$ is pyridyl optionally substituted with 1, 2, or 3 $R_7$ groups. In some embodiments is a compound of Formula (Ic), wherein $R_6$ is phenyl substituted with 1, 2, or 3 $R_7$ groups. In some embodiments is a compound of Formula (Ic), wherein $R_6$ is pyridyl substituted with 1, 2, or 3 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 or 2 $R_7$ groups and each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 or 2 $R_7$ groups and each $R_7$ is independently selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 $R_7$ group and $R_7$ is selected from halogen, $C_{1-6}$alkyl, phenyl, and $C_{2-9}$heteroaryl, wherein $C_{1-6}$alkyl, phenyl, and $C_{2-9}$heteroaryl are optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 $R_7$ group and $R_7$ is selected from halogen, $C_{1-6}$alkyl, and phenyl, wherein $C_{1-6}$alkyl and phenyl is optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 $R_7$ group and $R_7$ is halogen. In some embodiments is a compound of Formula (Ic), wherein $R_6$ is pyridyl substituted with 1 $R_7$ group and $R_7$ is fluoro. In some embodiments is a compound of Formula (Ic), wherein $R_6$ is pyridyl substituted with 1 $R_7$ group and $R_7$ is $C_{1-6}$alkyl optionally substituted with one, two, or three groups independently selected from halogen. In some embodiments is a compound of Formula (Ic), wherein $R_6$ is pyridyl substituted with 1 $R_7$ group and $R_7$ is unsubstituted $C_{1-6}$alkyl. In some embodiments is a compound of Formula (Ic), wherein $R_6$ is pyridyl substituted with 1 $R_7$ group and $R_7$ is phenyl optionally substituted with one, two, or three groups independently selected from halogen, $C_{1-6}$alkyl, $C_{1-6}$haloalkyl, $C_{1-6}$alkoxy, and $C_{1-6}$haloalkoxy. In some embodiments is a compound of Formula (Ic), wherein $R_6$ is pyridyl substituted with 1 $R_7$ group and $R_7$ is unsubstituted phenyl.

In some embodiments is a compound of Formula (Ic), wherein $R_6$ is unsubstituted pyridyl.

In some embodiments is a compound of Formula (Ic), wherein $R_2$, $R_3$, $R_4$, and $R_5$ are each hydrogen. In some embodiments is a compound of Formula (Ic), wherein $R_2$, $R_3$, $R_4$, and $R_5$ are each deuterium. In some embodiments is a compound of Formula (Ic), wherein $R_2$ is —OH, and $R_3$, $R_4$, and $R_5$ are each hydrogen. In some embodiments is a compound of Formula (Ic), wherein $R_3$ is —OH, and $R_2$, $R_4$, and $R_5$ are each hydrogen. In some embodiments is a compound of Formula (Ic), wherein $R_2$ and $R_4$ are each —OH, and $R_3$ and $R_5$ are each hydrogen. In some embodiments is a compound of Formula (Ic), wherein $R_2$ and $R_5$ are each —OH, and $R_3$ and $R_4$ are each hydrogen. In some embodiments is a compound of Formula (Ic), wherein $R_3$ and $R_4$ are each —OH, and $R_2$ and $R_5$ are each hydrogen. In some embodiments is a compound of Formula (Ic), wherein $R_3$ and $R_5$ are each —OH, and $R_2$ and $R_4$ are each hydrogen.

In some embodiments is a compound, or a pharmaceutically acceptable salt or solvate thereof, selected from:

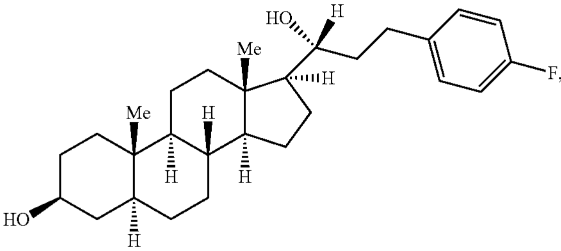

,

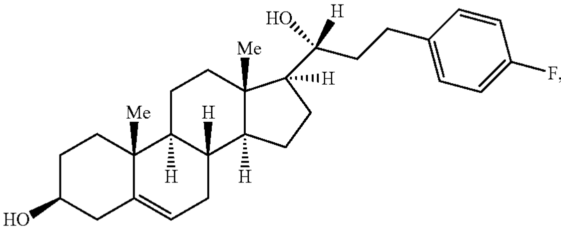

,

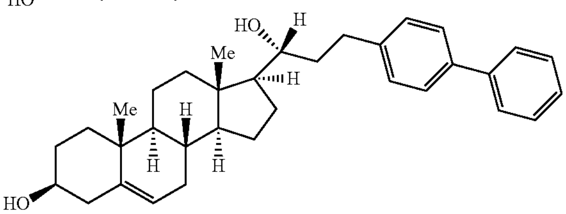

,

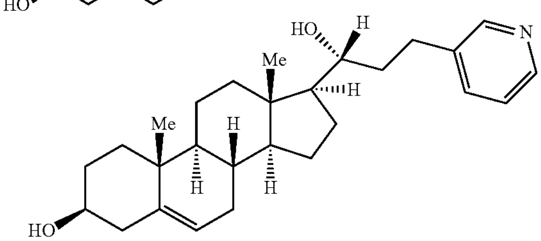

,

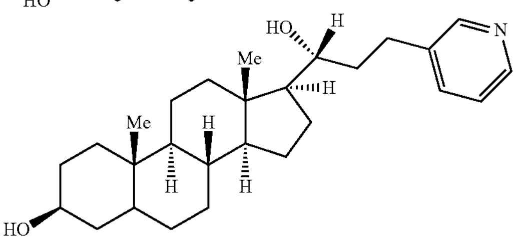

, and

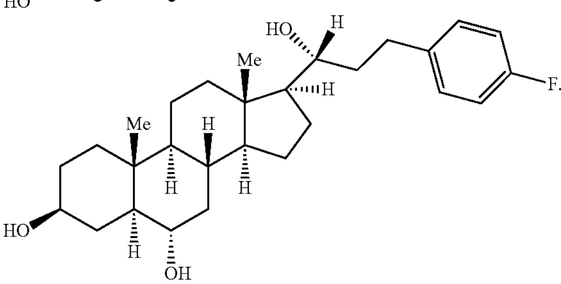

.

In some embodiments is a compound, or a pharmaceutically acceptable salt or solvate thereof, selected from:

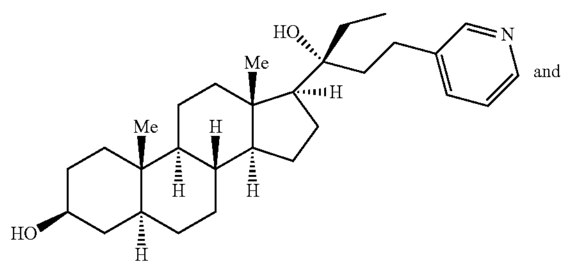

and

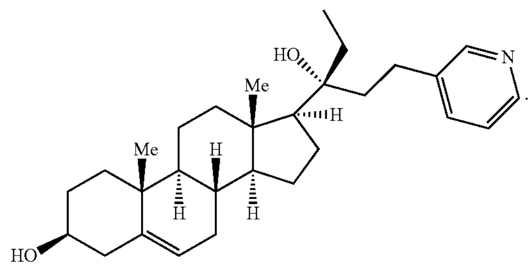

.

In some embodiments is a compound, or a pharmaceutically acceptable salt or solvate thereof, selected from:

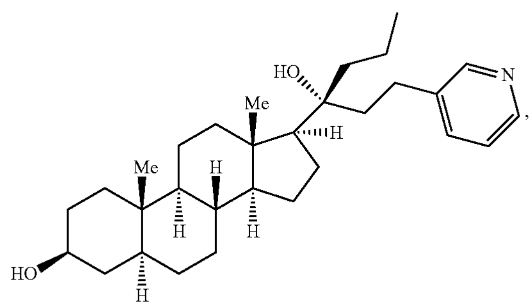

,

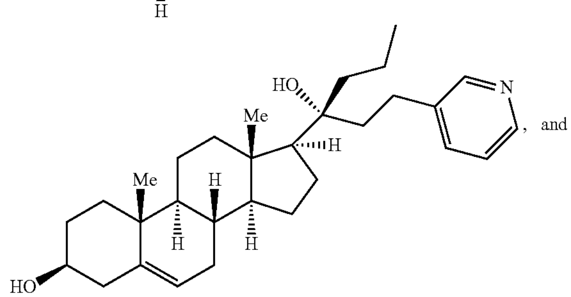

, and

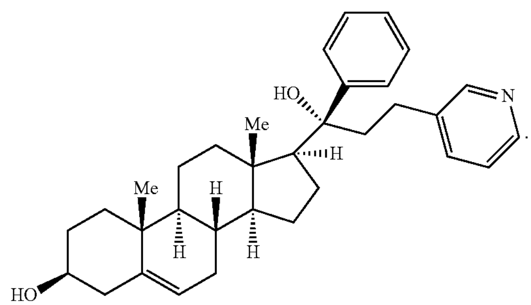

.

In some embodiments is a compound, or a pharmaceutically acceptable salt or solvate thereof, having the structure:

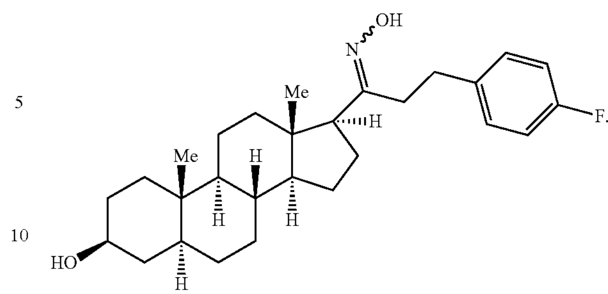

.

Further provided herein are pharmaceutical compositions comprising a compound of Formula (I), (Ia), (Ib), or (Ic) described herein, or a pharmaceutically acceptable salt or solvate thereof, and a pharmaceutically acceptable excipient. In some embodiments is a pharmaceutical composition comprising a compound of Formula (I), or a pharmaceutically acceptable salt or solvate thereof, and a pharmaceutically acceptable excipient. In some embodiments is a pharmaceutical composition comprising a compound of Formula (Ia), or a pharmaceutically acceptable salt or solvate thereof, and a pharmaceutically acceptable excipient. In some embodiments is a pharmaceutical composition comprising a compound of Formula (Ib), or a pharmaceutically acceptable salt or solvate thereof, and a pharmaceutically acceptable excipient. In some embodiments is a pharmaceutical composition comprising a compound of Formula (Ic), or a pharmaceutically acceptable salt or solvate thereof, and a pharmaceutically acceptable excipient.

Methods of Use

In some embodiments is a method of modulating Hedgehog signaling in a mammal, comprising administering to the mammal a compound of Formula (I), (Ia), (Ib), or (Ic) described herein, or a pharmaceutically acceptable salt or solvate thereof. In some embodiments is a method of modulating Hedgehog signaling in a mammal, comprising administering to the mammal a compound method of modulating Hedgehog signaling in a mammal, comprising administering to the mammal a compound of Formula (Ia), or a pharmaceutically acceptable salt or solvate thereof. In some embodiments is a method of modulating Hedgehog signaling in a mammal, comprising administering to the mammal a compound of Formula (Ib), or a pharmaceutically acceptable salt or solvate thereof. In some embodiments is a method of modulating Hedgehog signaling in a mammal, comprising administering to the mammal a compound of Formula (Ic), or a pharmaceutically acceptable salt or solvate thereof.

In some embodiments is a method of positively modulating Hedgehog signaling in a mammal, comprising administering to the mammal a compound of Formula (I), (Ia), (Ib), or (Ic) described herein, or a pharmaceutically acceptable salt or solvate thereof. In some embodiments is a method of positively modulating Hedgehog signaling in a mammal, comprising administering to the mammal a compound method of modulating Hedgehog signaling in a mammal, comprising administering to the mammal a compound of Formula (Ia), or a pharmaceutically acceptable salt or solvate thereof. In some embodiments is a method of positively modulating Hedgehog signaling in a mammal, comprising administering to the mammal a compound of Formula (Ib), or a pharmaceutically acceptable salt or solvate thereof. In some embodiments is a method of positively modulating Hedgehog signaling in a mammal, comprising administering to the mammal a compound of Formula (Ic), or a pharmaceutically acceptable salt or solvate thereof.

In some embodiments is a method of negatively modulating Hedgehog signaling in a mammal, comprising administering to the mammal a compound of Formula (I), (Ia), (Ib), or (Ic) described herein, or a pharmaceutically acceptable salt or solvate thereof. In some embodiments is a method of negatively modulating Hedgehog signaling in a mammal, comprising administering to the mammal a compound method of modulating Hedgehog signaling in a mammal, comprising administering to the mammal a compound of Formula (Ia), or a pharmaceutically acceptable salt or solvate thereof. In some embodiments is a method of negatively modulating Hedgehog signaling in a mammal, comprising administering to the mammal a compound of Formula (Ib), or a pharmaceutically acceptable salt or solvate thereof. In some embodiments is a method of negatively modulating Hedgehog signaling in a mammal, comprising administering to the mammal a compound of Formula (Ic), or a pharmaceutically acceptable salt or solvate thereof.

Synthesis of the Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

Routes of Administration

Suitable routes of administration include, but are not limited to, oral, intravenous, aerosol, parenteral, ophthalmic, pulmonary, transmucosal, transdermal, nasal, and topical administration. In addition, by way of example only, parenteral delivery includes intramuscular, subcutaneous, intravenous, intramedullary injections, as well as intrathecal, direct intraventricular, intraperitoneal, intralymphatic, and/or intranasal injections.

In some embodiments, a compound of Formula (I), (Ia), (Ib), or (Ic) is administered orally, intravenously, intraperitoneally, subcutaneously, or as an aerosol. In some embodiments, a compound of Formula (I), (Ia), (Ib), or (Ic) is administered orally, intravenously, intraperitoneally, or subcutaneously. In some embodiments, a compound of Formula (I), (Ia), (Ib), or (Ic) is administered orally. In some embodiments, a compound of Formula (I), (Ia), (Ib), or (Ic) is administered intravenously. In some embodiments, a compound of Formula (I), (Ia), (Ib), or (Ic) is administered intraperitoneally. In some embodiments, a compound of Formula (I), (Ia), (Ib), or (Ic) is administered subcutaneously. In some embodiments, a compound of Formula (I), (Ia), (Ib), or (Ic) is administered as an aerosol.

In certain embodiments, a compound of Formula (I), (Ia), (Ib), or (Ic) is administered in a local rather than systemic manner, for example, via topical application of the compound directly on to skin, or intravenously, or subcutaneously, often in a depot preparation or sustained release formulation. In specific embodiments, long acting formulations are administered by implantation (for example subcutaneously or intramuscularly) or by intramuscular injection. In yet other embodiments, the compound as described herein is provided in the form of a rapid release formulation, in the form of an extended release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Paennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (Ia), (Ib), or (Ic) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

The pharmaceutical formulations described herein are administered to a subject by appropriate administration routes, including but not limited to, oral, parenteral (e.g., intravenous, subcutaneous, intramuscular), intranasal, buccal, topical, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (Ib), or (Ic) are manufactured in a conventional manner, such as, by way of example only, by means of conventional mixing, dissolving, granulating, dragee-making, levigating, emulsifying, encapsulating, entrapping or compression processes.

In some embodiments, compounds of Formula (I), (Ia), (Ib), or (Ic) exist in unsolvated form or in solvated forms with pharmaceutically acceptable solvents such as water, ethanol, and the like. The solvated forms of the compounds of Formula (I), (Ia), (Ib), or (Ic) are also considered to be disclosed herein. In some embodiments, the compounds of Formula (I), (Ia), (Ib), or (Ic) exist as tautomers. All tautomers are included within the scope of the compounds presented herein.

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein, which include a compound of Formula (I), (Ia), (Ib), or (Ic) are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Certain Systemically Administered Compositions

In one aspect, a compound of Formula (I), (Ia), (Ib), or (Ic) is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multidose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a compound of Formula (I), (Ia), (Ib), or (Ic) is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Representative intranasal formulations are described in, for example, U.S. Pat. Nos. 4,476,116, 5,116,817 and 6,391,452. Formulations that include a compound of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

In some embodiments, pharmaceutical formulations of a compound of Formula (I), (Ia), (Ib), or (Ic) are in the form of a capsules, including push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added. A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration.

In one aspect, solid oral dosage forms are prepared by mixing a compound of Formula (I), (Ia), (Ib), or (Ic) with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder.

Compressed tablets are solid dosage forms prepared by compacting the bulk blend of the formulations described above. In various embodiments, tablets will include one or more flavoring agents.

In other embodiments, the tablets will include a film surrounding the final compressed tablet. In some embodiments, the film coating can provide a delayed release of the compound of Formula (I), (Ia), (Ib), or (Ic) from the formulation. In other embodiments, the film coating aids in patient compliance (e.g., Opadry® coatings or sugar coating). Film coatings including Opadry® typically range from about 1% to about 3% of the tablet weight.

In some embodiments, solid dosage forms, e.g., tablets, effervescent tablets, and capsules, are prepared by mixing particles of a compound with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to a Hedgehog signaling inhibitor, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a compound of Formula (I), (Ia), (Ib), or (Ic) are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a Hedgehog signaling inhibitor is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a compound of Formula (I), (Ia), (Ib), or (Ic) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), (Ia), (Ib), or (Ic) is formulated to include one or more pharmaceutical excipients and flavors. Such a powder is prepared, for example, by mixing the compound and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

EXAMPLES

The following specific examples are to be construed as merely illustrative, and not limitative of the remainder of the disclosure in any way whatsoever.

All synthetic chemistry was performed in standard laboratory glassware unless indicated otherwise in the examples. Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized.

Example 1: Synthesis of (3S,8S,9S,10R,13S,14S,17S)-17-((R)-3-(4-fluorophenyl)-1-hydroxypropyl)-10,13-dimethyl-2,3,4,7,8,9,10,11,12,13,14,15,16,17-tetradecahydro-1H-cyclopenta[a]phenanthren-3-ol (Compound 1)

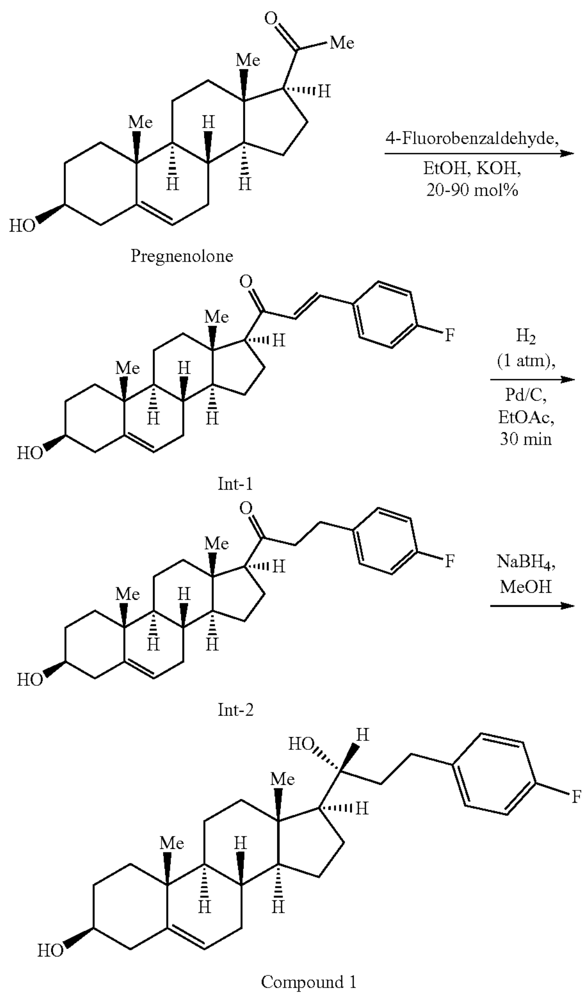

Pregnenolone

Int-1

Int-2

Compound 1

Step 1: Pregnenolone (20 g, 63 mmol) was suspended in ethanol (300 mL) at room temperature. Potassium hydroxide solution (4M, 31 mL, 2 equivalents) was added to the reaction mixture followed by addition of 4-fluorobenzaldehyde (10 mL, 93 mmol, 1.5 equivalents). The resulting mixture was stirred at room temperature for 24 hours. Water (400 mL) was then added to the reaction mixture to precipitate the product. The crude solid product was isolated using vacuum filtration, washed with water (2×200 mL), and then air dried to afford (E)-3-(4-fluorophenyl)-1-((3S,8S,9S,10R,13S,14S,17S)-3-hydroxy-10,13-dimethyl-2,3,4,7,8,9,10,11,12,13,14,15,16,17-tetradecahydro-1H-cyclopentaral-phenanthren-17-yl)prop-2-en-1-one (Int-1) (26.7 g), which was used without further purification.

Step 2: Int-1 (0.25 g, 0.59 mmol) was dissolved in ethyl acetate (10 mL) at room temperature and palladium on carbon catalyst (25 mg) was added to the mixture. The atmosphere in the reaction flask was purged three times with hydrogen gas using a balloon. The reaction mixture was then stirred at room temperature under a hydrogen atmosphere. After 30 min, the mixture was filtered over celite and concentrated in vacuo to yield 3-(4-fluorophenyl)-1-((3S,5S,8R,9S,10S,13S,14S,17S)-3-hydroxy-10,13-dimethyl-hexadecahydro-1H-cyclopenta[a]phenanthren-17-yl) propan-1-one (Int-2) (0.24 g), which was used without further purification.

Step 3: Int-2 (77 mg, 0.18 mmol) was dissolved in tetrahydrofuran (1 mL) at room temperature and cooled to 0° C. Sodium borohydride (15 mg, 0.40 mmol) was added portionwise to the reaction mixture at 0° C. The reaction mixture was then stirred at 0° C. for 1 hour and then most of the methanol was evaporated. The mixture was diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered, and concentrated in vacuo. The crude mixture was purified via automated chromatography (ISCO) to yield (3S,8S,9S,10R,13S,14S,17S)-17-((R)-3-(4-fluorophenyl)-1-hydroxypropyl)-10,13-dimethyl-2,3,4,7,8,9,10,11,12,13,14,15,16,17-tetradecahydro-1H-cyclopenta[a]phenanthren-3-ol (Compound 1) (50 mg, 64%). $^{1}$H NMR ($CDCl_3$, 400 MHZ) δ 7.14-7.11 (2H, m), 6.97 (2H, m), 5.33 (1H, m), 3.61-3.49 (2H, m), 2.73-2.44 (2H, m), 2.01 (2H, m), 1.81-0.52 (20H, m), 0.99 (3H, m), 0.70 (3H, m); $^{13}$C NMR ($CDCl_3$, 100 MHZ) δ 161.2, (d, J=242 Hz), 140.8, 138.2 (d, J=3.1), 129.6, (d, J=20 Hz), 121.8, 121.6, 115.1 (d, J=20 Hz), 73.8, 71.8, 56.7, 56.2, 50.1, 42.4, 42.3, 40.0, 38.9, 37.3, 36.6, 31.9, 31.7, 31.7, 30.9, 25.5, 24.6, 21.0, 19.4, 12.4.

Example 2: Synthesis of (3S,5S,8R,9S,10S,13S,14S,17S)-17-((R)-3-(4-fluorophenyl)-1-hydroxypropyl)-10,13-dimethylhexadecahydro-1H-cyclopenta[a]phenanthren-3-ol (Compound 2)

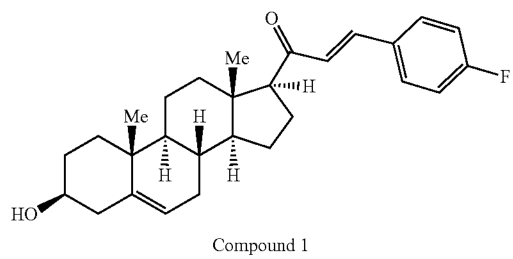

Compound 1

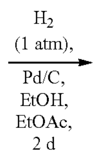

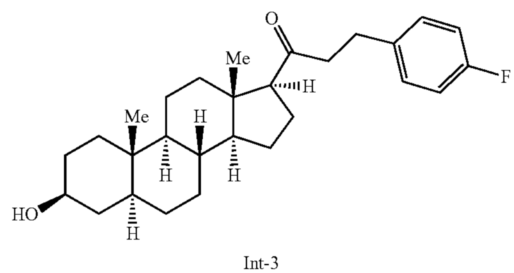

Int-3

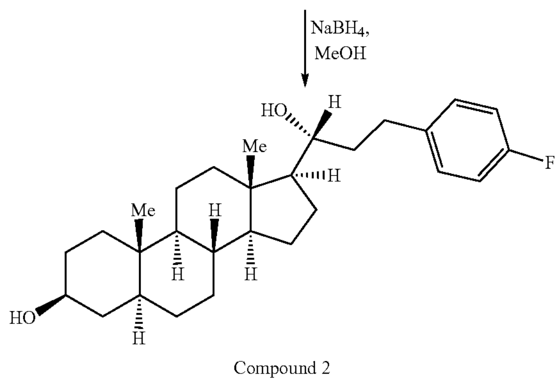

Compound 2

Step 1: Compound 1 (25 g, 59 mmol) was dissolved in ethanol (300 mL) and ethyl acetate (100 mL) at room temperature and palladium on carbon catalyst (2.5 g) was added to the mixture. The atmosphere in the reaction flask was purged three times with hydrogen gas using a balloon. The reaction mixture was then stirred at room temperature under a hydrogen atmosphere. After 2 days, the mixture was filtered over celite and concentrated in vacuo to yield a crude solid. The crude product was dissolved in a minimal volume of hot ethyl acetate and allowed to crystallize overnight. The mother liquor was then removed from the crystalline solid by decantation to afford 3-(4-fluorophenyl)-1-((3S,5S,8R,9S,10S,13S,14S,17S)-3-hydroxy-10,13-dimethylhexadecahydro-1H-cyclopenta[a]phenanthren-17-yl) propan-1-one (Int-3) (17 g, 68%).

Step 2: Int-3 (0.15 g, 0.35 mmol) was dissolved in methanol (7 mL) at room temperature and cooled to 0° C. Sodium borohydride (20 mg, 0.52 mmol) was added portionwise to the reaction mixture at 0° C. The reaction mixture was stirred at 0° C. for 1 hour and then most of the methanol was evaporated. The mixture was diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered, and concentrated in vacuo. The crude mixture was purified via automated chromatography (ISCO) to yield (3S,5S,8R,9S,10S,13S,14S,17S)-17-((R)-3-(4-fluorophenyl)-1-hydroxypropyl)-10,13-dimethylhexadecahydro-1H-cyclopenta[a]phenanthren-3-ol (Compound 2) (0.12 g, 80%). $^{1}H$ NMR ($CDCl_3$, MeOD, 400 MHZ) δ 7.14-7.11 (2H, m), 6.97 (2H, m), 3.61-3.49 (2H, m), 2.73-2.44 (2H, m), 2.01 (2H, m), 1.81-0.52 (22H, m), 0.78 (3H, m), 0.70 (3H, m); $^{13}C$ NMR ($CDCl_3$, MeOD, 100 MHZ) δ 161.2, (d, J=242 Hz), 140.8, 138.2 (d, J=3.1), 129.6, (d, J=20 Hz), 121.6, 115.1 (d, J=20 Hz), 73.3, 70.8, 56.5, 55.9, 54.3, 44.8, 42.5, 39.9, 38.7, 37.7, 36.9, 35.4, 35.3, 32.0, 31.0, 30.8, 28.6, 25.4, 24.4, 21.1, 12.3, 12.1.

Example 3: Synthesis of (3S,8S,9S,10R,13S,14S,17S)-17-((R)-3-([1,1'-biphenyl]-4-yl)-1-hydroxypropyl)-10,13-dimethyl-2,3,4,7,8,9,10,11,12,13,14,15,16,17-tetradecahydro-1H-cyclopenta[a]phenanthren-3-ol (Compound 3)

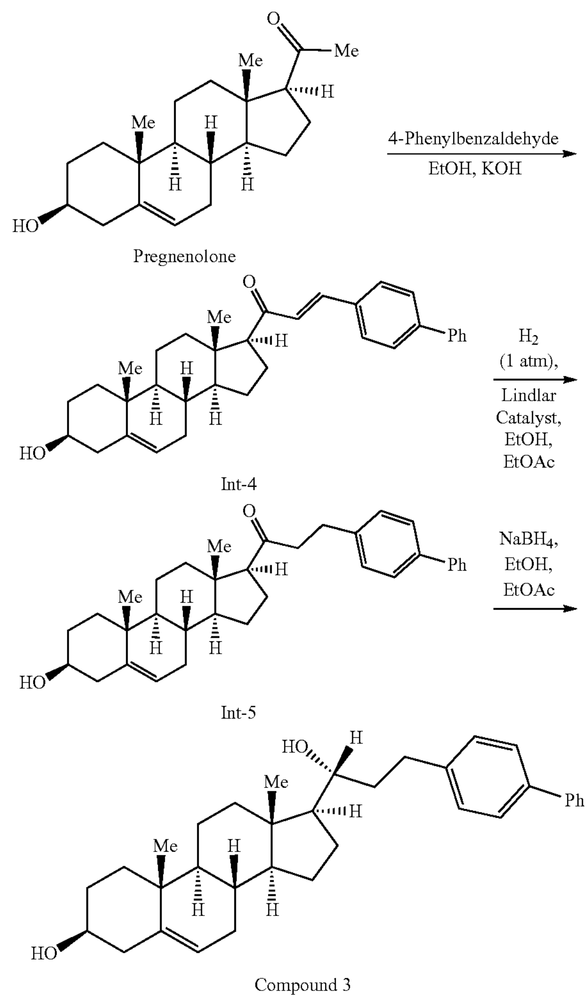

Pregnenolone

Int-4

Int-5

Compound 3

Step 1: Pregnenolone (1 g, 3 mmol) was suspended in ethanol (30 mL) at room temperature. Potassium hydroxide solution (4M, 2 mL) was added to the reaction mixture followed by addition of 4-phenylbenzaldehyde (660 mg, 3.5 mmol, 1.2 equivalents). The resulting mixture was stirred at room temperature for 24 hours. Water (40 mL) was then added to the reaction mixture to precipitate the product. The crude solid product was isolated using vacuum filtration, washed with water (2×10 mL), and then air dried to afford (E)-3-([1,1'-biphenyl]-4-yl)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)prop-2-en-1-one (Int-4) (1.5 g), which was used without further purification.

Step 2: Int-4 (0.48 g, 1 mmol) was suspended in ethanol (4 mL) and ethyl acetate (4 mL) at room temperature and Lindlar catalyst (48 mg) was added to the mixture. The atmosphere in the reaction flask was purged three times with hydrogen gas using a balloon. The reaction mixture was then stirred at room temperature under a hydrogen atmosphere. After 2 days, the mixture was filtered over celite and concentrated in vacuo to yield the crude ketone. The crude ketone product was dissolved in a minimal volume of hot ethyl acetate and allowed to crystallize overnight. The mother liquor was then removed from the crystalline solid by decantation to yield 3-([1,1'-biphenyl]-4-yl)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)propan-1-one (Int-5) (0.4 g, 83%).

Step 3: Int-5 (0.10 g, 0.2 mmol) was dissolved in ethanol (2 mL) and ethyl acetate (2 mL) at room temperature and cooled to 0° C. Sodium borohydride (20 mg, 0.52 mmol) was added portionwise to the reaction mixture at 0° C. The reaction mixture was stirred at 0° C. for 1 hour and then most of the methanol was evaporated. The mixture further diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered, and concentrated in vacuo. The crude mixture was purified via automated chromatography (ISCO) to yield (3S,8S,9S,10R,13S,14S,17S)-17-((R)-3-([1,1'-biphenyl]-4-yl)-1-hydroxypropyl)-10,13-dimethyl-2,3,4,7,8,9,10,11,12,13,14,15,16,17-tetradecahydro-1H-cyclopenta[a]phenanthren-3-ol (Compound 3) (0.08 g, 80%). $^{1}H$ NMR ($CDCl_3$, 400 MHZ) δ 7.61-7.21 (10H, m), 5.37 (1H, m), 3.64 (1H, dd, J=7.9, 2.4 Hz), 3.53 3 (1H, ddd, J=15.9, 11.0, 4.8 Hz), 2.96-2.85 (1H, m), 2.75-2.64 (1H, m), 2.34-2.19 (2H, m), 2.15-1.78 (5H, m), 2.34-2.19 (5H, m), 1.73-1.38 (11H, m), 1.34-0.92 (6H, m), 1.02 (3H), 0.78 (3H); $^{13}C$ NMR ($CDCl_3$, 100 MHZ) δ 141.7, 141.1, 140.9, 138.7, 128.9, 128.8, 128.7, 127.3, 127.2, 127.0, 127.0, 126.9, 126.9, 121.5, 74.0, 71.8, 56.7, 51.2, 50.2, 42.4, 42.3, 40.0, 38.8, 37.3, 36.6, 31.9, 31.8, 31.7, 31.4, 25.5, 24.6, 21.0, 19.4, 12.4.

Example 4: Synthesis of (3S,8S,9S,10R,13S,14S,17S)-17-((R)-1-hydroxy-3-(pyridinyl)propyl)-10,13-dimethyl-2,3,4,7,8,9,10,11,12,13,14,15,16,17-tetradecahydro-1H-cyclopenta[a]phenanthren-3-ol (Compound 4a)

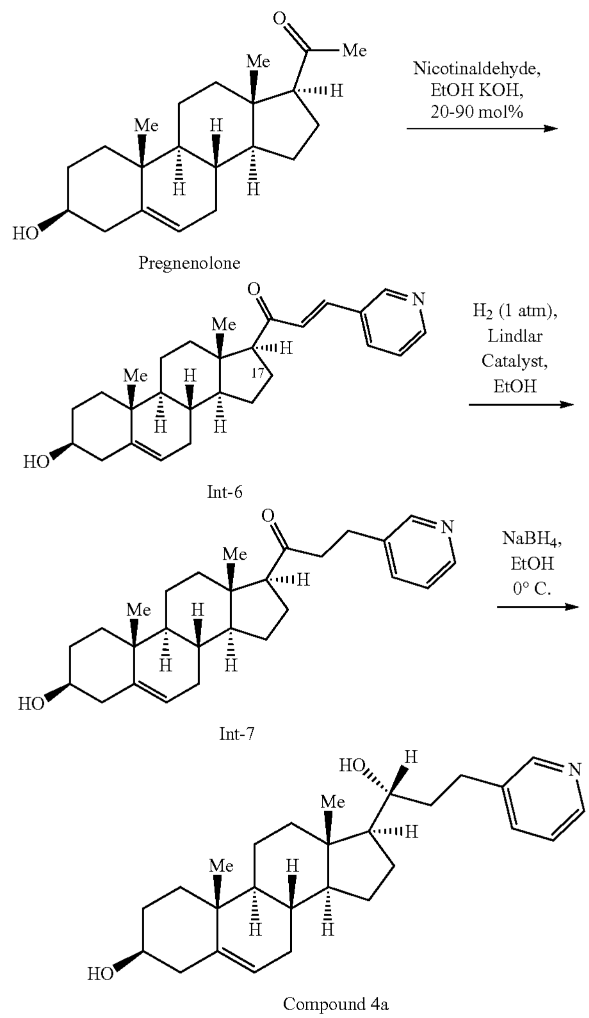

Pregnenolone

Int-6

Int-7

Compound 4a

Step 1: Pregnenolone (5.0 g, 16 mmol) was suspended in ethanol (80 mL) at room temperature. A sub-stoichiometric amount of potassium hydroxide solution (4M, 2 mL, 0.5 equivalents) was added to the reaction mixture followed by addition of nicotinaldehyde (1.78 mL, 19 mmol). The resulting mixture was stirred at room temperature for 24 hours. Water (100 mL) was then added to the reaction mixture to precipitate the product. The crude solid product was isolated using vacuum filtration, washed with water (2×50 mL), and then air dried. The crude product was purified to remove minor amounts of undesired C-17 epimer. The crude product was suspended in 1:1 hexane/ethyl acetate (25 mg/mL) and sonicated for several minutes. The undesired C-17 epimer was then removed by heating the mixture to reflux temperature for 10 mins followed by hot filtration to afford (E)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)-3-(pyridin-3-yl)prop-2-en-1-one (Int-6) (6.68 g, 67%). $^1H$ NMR ($CDCl_3$, 400 MHZ) δ 8.75 (1H, d, J=2 Hz), 8.57 (1H, dd, J=5, 2 Hz), 7.86-7.81 (1H, m), 7.50 (1H, d, J=17 Hz), 7.31 (1H, dd, J=8, 4 Hz), 6.81 (1H, d, J=17 Hz), 5.38-5.30 (1H, m), 3.56-3.40 (1H, m), 2.83 (1H, dd, J=9, 9 Hz), 2.39-2.17 (3H, m), 2.06-1.95 (3H, m), 1.87-1.01 (13H, m), 0.98 (3H, s), 0.63 (3H, s); $^{13}C$ NMR ($CDCl_3$, 100 MHZ) δ 199.9, 150.3, 149.8, 140.9, 137.6, 134.6, 130.7, 128.5, 123.8, 121.3, 71.6, 62.3, 57.2, 50.0, 45.1, 42.3, 39.2, 37.3, 36.5, 32.0, 31.8, 31.6, 24.7, 22.7, 21.1, 19.4, 13.5.

Step 2: Int-6 (4.0 g, 10 mmol) was suspended in ethanol (150 mL) at room temperature and Lindlar's catalyst (0.4 g) was added to the mixture. The atmosphere in the reaction flask was purged three times with hydrogen gas using a balloon. The reaction mixture was then stirred at room temperature under a hydrogen atmosphere. After 2 days, the mixture was filtered over celite and concentrated in vacuo to yield the crude ketone (4.0 g of recovery). The crude ketone product was dissolved in a minimal volume of hot ethyl acetate (heat gun) and allowed to crystallize overnight. The mother liquor was then removed from the crystalline solid by decantation to afford 1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)(pyridin-3-yl)propan-1-one (Int-7) (3.5 g). $^1H$ NMR ($CDCl_3$, 400 MHZ) δ 8.42 (1H, d, J=2 Hz), 8.40 (1H, dd, J=5.1 Hz), 7.52-7.47 (1H, m), 7.17 (1H, dd, J=8, 5 Hz), 5.33-5.26 (1H, m), 3.54-3.44 (1H, m), 2.92-2.91 (2H, m), 2.72-2.64 (2H, m), 2.45, (1H, dd, J=9, 9 Hz), 2.35-1.00 (17H, m), 0.96 (3H, s), 0.52 (3H, s); $^{13}C$ NMR ($CDCl_3$, 100 MHZ) δ 209.7, 149.7, 147.4, 140.8, 136.8, 136.2 123.3, 121.1, 71.4, 63.0, 56.9, 49.9, 45.3, 44.3, 42.2, 38.9, 37.2, 36.4, 31.8, 31.7, 31.5, 26.7, 24.4, 23.0, 21.0, 19.3, 13.3.

Step 3: Int-7 (0.12 g, 0.3 mmol) was dissolved in ethanol (3 mL) at room temperature and cooled to 0° C. Sodium borohydride (20 mg, 0.52 mmol) was added portionwise to the reaction mixture at 0° C. The reaction mixture was stirred at 0° C. for 1 hour and then most of the methanol was evaporated. The mixture was diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered, and concentrated in vacuo. The crude mixture was purified via automated chromatography (ISCO) to yield (3S,8S,9S,10R,13S,14S,17S)-17-((R)-1-hydroxy-3-(pyridin-3-yl)propyl)-10,13-dimethyl-2,3,4,7,8,9,10,11,12,13,14,15,16,17-tetradecahydro-1H-cyclopenta[a]phenanthren-3-ol (Compound 4a) (0.1 g, 80%). $^1H$ NMR ($CDCl_3$, 400 MHZ) δ 8.47 (1H, d, J=1 Hz), 8.45 (1H, dd, J=5, 2 Hz), 7.53-7.48 (1H, m), 7.23-7.18 (1H, m), 5.35-5.31 (1H, m), 3.62-3.47 (2H, m), 2.97-2.58 (2H, m), 2.31-2.15 (2H, m), 2.12-1.92 (2H, m), 1.90-1.72 (7H, m), 1.69-1.36 (6H, m), 1.33-0.89 (6H, m), 1.01 (3H, s), 0.76 (3H, m); $^{13}C$ NMR ($CDCl_3$, 100 MHZ) δ 149.9, 147.2, 140.9, 137.8, 136.0, 123.4, 121.5, 73.6, 71.7, 56.7, 56.2, 50.1, 42.4, 42.3, 40.1, 38.8, 37.3, 36.5, 31.9, 31.7, 31.6, 28.9, 25.4, 24.5, 21.0, 19.4, 12.4.

Example 5: Synthesis of (3S,5S,6S,8S,9S,10R,13S,14S,17S)-17-((R)-3-(4-fluorophenyl)-1-hydroxypropyl)-10,13-dimethylhexadecahydro-1H-cyclopenta[a]phenanthrene-3,6-diol (Compound 5)

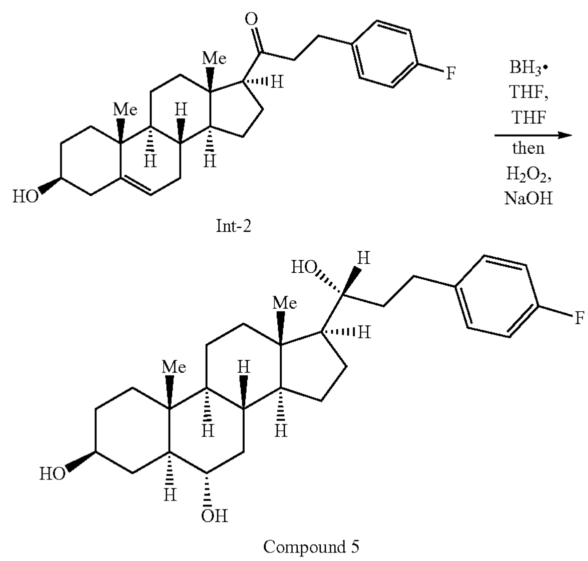

Int-2

Compound 5

Int-2 (0.4 g, 0.9 mmol) was dissolved in dry THF (5 mL) at room temperature and cooled to 0° C. under $N_2$-atmosphere. A solution of borane THF complex in THF (4 mL, 4 equivalents) was added dropwise to the reaction mixture at 0° C. The reaction mixture was then stirred at room temperature for 3 hours. Sodium hydroxide solution (1 M, 10 mL) and hydrogen peroxide (30%, 15 mL) were slowly added sequentially. The resulting mixture then was stirred for one hour at room temperature, diluted with $CH_2Cl_2$ (40 mL), transferred to a separatory funnel, and washed with deionized water (1×80 mL). The organic layer was separated, dried with sodium sulfate, filtered, and concentrated. The crude mixture was purified via automated chromatography (ISCO) to yield (3S,5S,6S,8S,9S,10R,13S,14S,17S)-17-((R)-3-(4-fluorophenyl)-1-hydroxypropyl)-10,13-dimethylhexadecahydro-1H-cyclopenta[a]phenanthrene-3,6-diol (Compound 5) (0.20 g, 50%). $^1$H NMR (MeOD, 400 MHZ) δ 7.21 (2H, m), 7.01 (2H, m), 3.44 (2H, m), 3.21 (1H, m) (2.73-2.54 (3H, m), 2.2 (3H, m), 1.81-0.83 (18H, m), 0.77 (3H, s), 0.70 (3H, s), 0.52 (2H, m); $^{13}$C NMR (MeOD, 100 MHZ) δ 161.2, (d, J=242 Hz), 139.4, 130.4 (d, J=3.1), 115.1 (d, J=20 Hz), 72.0, 70.1, 67.9, 56.3, 56.0, 54.2, 51.9, 42.7, 42.4, 39.2, 37.6, 34.2, 32.9, 31.7, 30.8, 25.6, 24.7, 21.1, 13.7, 12.6.

A 5 mg portion of Compound 5 was dissolved in ethanol (0.5 mL) and placed in the back of a fume hood overnight for slow evaporation of the solvent. Single crystal X-ray diffraction data were collected at 100K on a diffractometer with Bruker Apex-II CCD detector and a Cu-micro focus source. Crystal data: Orthorhombic, a=7.5542(5) Å, b=10.8760(7) Å, c=34.071(2) Å, α=90° β=90°, γ=90°, Vol.=2799.3(3) Å$^3$, Space group=$P2_12_12_1$. The final anisotropic full matrix least-squares refinement on $F^2$ converged at $R_1$=0.041, $wR_2$=0.086, GOF=1.03. An atomic displacement ellipsoid drawing of Compound 5 is shown in FIG. 4.

Example 6: Synthesis of (3S,5S,8R,9S,10S,13S,14S,17S)-17-((R)-3-hydroxy-1-(pyridin-3-yl)pentan-3-yl)-10,13-dimethylhexadecahydro-1H-cyclopenta[a]phenanthren-3-ol (Compound 6)

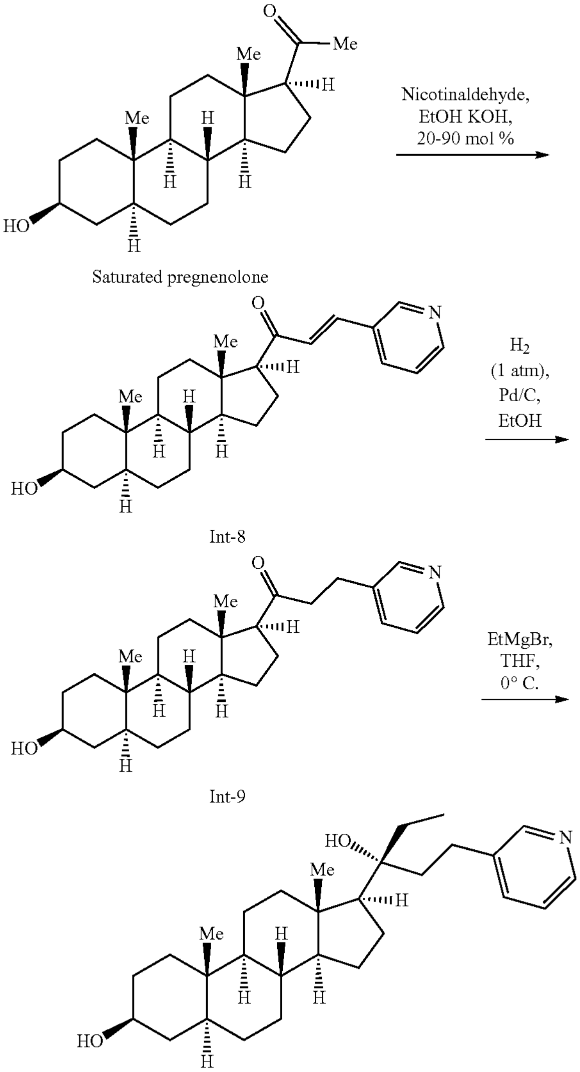

Saturated pregnenolone

Int-8

Int-9

Compound 6

Saturated pregnenolone (1.2 g, 3.8 mmol) was suspended in ethanol (20 mL) at room temperature. A potassium hydroxide solution (4M, 0.2 mL, 0.2 equivalents) was added to the reaction mixture followed by addition of nicotinaldehyde (0.7 g, 6.5 mmol). The resulting mixture was stirred at room temperature for 24 hours. Water (50 mL) was then added to the reaction mixture to precipitate the product. The crude solid product was isolated using vacuum filtration, washed with water (2×20 mL), and then air dried to afford 1.56 g (>95%) of (E) ((3S,5S,8R,9S,10S,13S,14S,17S)-3-hydroxy-10,13-dimethylhexadecahydro-1H-cyclopenta[a]phenanthren-1'7-yl)-3-(pyridin-3-yl)prop-2-en-1-one (Int-8). $^1$H NMR (400 MHz, $CDCl_3$) δ 8.75 (1H, d, J=2 Hz), 8.57 (1H, dd, J=5, 2 Hz), 7.86-7.81 (1H, m), 7.50 (1H, d, J=17 Hz), 7.31 (1H, dd, J=8, 4 Hz), 6.81 (1H, d, J=17 Hz), 3.56-3.40 (1H, m), 2.83 (1H, dd, J=9, 9 Hz), 2.39-2.17 (3H, m), 2.06-1.95 (3H, m), 1.87-1.01 (14H, m), 0.81 (3H, s), 0.62 (3H, s).

Int-8 (1.5 g, 3.8 mmol) was suspended in ethanol (25 mL) and ethyl acetate (5 mL) at room temperature and palladium on carbon catalyst (0.15 g) was added to the mixture. The atmosphere in the reaction flask was purged three times with hydrogen gas using a balloon. The reaction mixture was then stirred at room temperature under a hydrogen atmosphere. After 2 days, the mixture was filtered over celite and concentrated in vacuo. The crude product mixture was purified via automated chromatography (ISCO) to yield 1-((3S,5S,8R,9S,10S,13S,14S,17S)-3-hydroxy-10,13-dimethylhexadecahydro-1H-cyclopenta[a]phenanthren-17-yl)-3-(pyridin-3-yl)propan-1-one (Int-9) (1.0 g, 66%). $^1$H NMR (400 MHz, $CDCl_3$) δ 8.42 (1H, d, J=2 Hz), 8.40 (1H, dd, J=5.1 Hz), 7.52-7.47 (1H, m), 7.17 (1H, dd, J=8, 5 Hz), 3.54-3.44 (1H, m), 2.92-2.91 (2H, m), 2.72-2.64 (2H, m), 2.45, (1H, dd, J=9, 9 Hz), 2.35-1.00 (17H, m), 0.96 (3H, s), 0.52 (3H, s).

Int-9 (0.41 g, 1 mmol) was dissolved in dry tetrahydrofuran (5 mL) at room temperature and cooled to 0° C. under $N_2$-atmosphere. A solution of ethyl magnesium bromide (3 M in ether, 2 mL, 6 mmol) was added dropwise to the reaction mixture at 0° C. The reaction mixture was then stirred at 0° C. for 1 hour until the starting material was mostly consumed (TLC analysis). Then the reaction was carefully quenched with a small volume (~1 mL) of methanol and the mixture further diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered and concentrated in vacuo. The crude mixture was purified via automated chromatography (ISCO) running an ethyl acetate/methanol gradient (0-10%) to yield (3S,5S,8R,9S,10S,13S,14S,17S)-17-((R)-3-hydroxy-1-(pyridin-3-yl)pentan-3-yl)-10,13-dimethylhexadecahydro-1H-cyclopenta[a]phenanthren-3-ol (Compound 6) (0.35 g, 80%). $^1$H NMR (400 MHz, $CDCl_3$) δ 8.42 (1H, d, J=1 Hz), 8.38 (1H, dd, J=5, 2 Hz), 7.53-7.48 (1H, m), 7.23-7.18 (1H, m), 3.54 (1H, m), 2.69-2.63 (2H, m), 2.33-2.17 (2H, m), 2.05 (1H, m), 2.01-1.26 (17H, m), 1.22 (2H, m), 1.18-0.60 (6H, m), 0.85 (3H, s), 0.77 (3H, s); $^{13}$C NMR (100 MHz, $CDCl_3$) δ 149.1, 146.6, 138.5, 136.4, 123.6, 77.3, 71.2, 56.8, 55.3, 54.3, 44.9, 43.0, 40.7, 38.8, 38.2, 37.0, 35.4, 34.8, 32.0, 31.5, 31.0, 28.7, 27.3, 23.6, 22.3, 21.1, 13.8, 12.3, 8.4.

Example 7: Synthesis of (3S,5S,8R,9S,10S,13S,14S,17S)-17-((R)-1-hydroxy-3-(pyridinyl)propyl)-10,13-dimethylhexadecahydro-1H-cyclopenta[a]phenanthren-3-ol (Compound 4b)

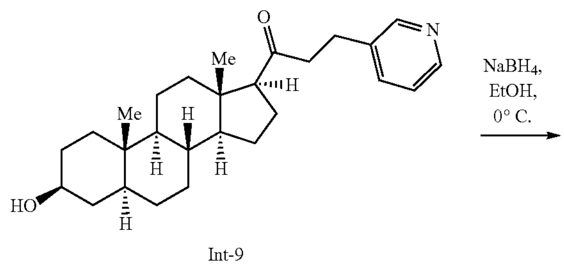

Int-9

-continued

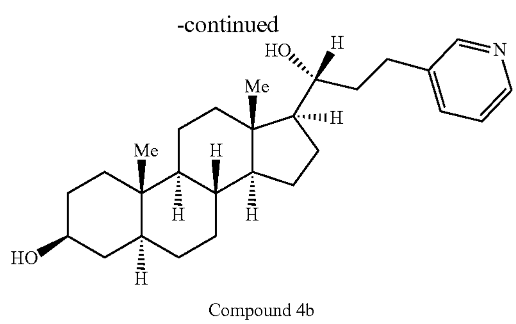

Compound 4b

Int-9 (0.12 g, 0.3 mmol) was dissolved in ethanol (3 mL) at room temperature and cooled to 0° C. (ice bath). Sodium borohydride (20 mg, 0.52 mmol) was added portionwise to the reaction mixture at 0° C. The reaction mixture was then stirred at 0° C. for 1 hour. Then most of the methanol was evaporated and the mixture further diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered, and concentrated in vacuo. The crude mixture was purified via automated chromatography (ISCO) to yield (3S,5S,8R,9S,10S,13S,14S,17S)-17-((R)-1-hydroxy-3-(pyridin-3-yl)propyl)-10,13-dimethylhexadecahydro-1H-cyclopenta[a]phenanthren-3-ol (0.1 g, 80%) (Compound 4b). $^1$H NMR (400 MHz, $CDCl_3$) δ 8.43 (2H, m), 7.56-7.50 (1H, m), 7.26-7.20 (1H, m), 3.62-3.47 (2H, m), 2.97-2.58 (2H, m), 2.78-2.63 (2H, m), 2.04-0.84 (m 23H), 0.80 (3H, s), 0.72 (3H, s); $^{13}$C NMR (100 MHz, $CDCl_3$) δ 149.2, 146.5, 136.0, 124.9, 123.7, 123.7, 73.6, 71.4, 56.9, 55.9, 54.4, 44.8, 42.7, 40.3, 38.2, 37.0, 35.5, 35.3, 32.1, 31.5, 28.9, 28.7, 25.5, 21.2, 12.7, 12.4.

Example 8: Synthesis of (3S,8S,9S,10R,13S,14S,17S)-17-((R)-3-hydroxy-1-(pyridin-3-yl)pentan-3-yl)-10,13-dimethyl-2,3,4,7,8,9,10,11,12,13,14,15,16,17-tetradecahydro-1H-cyclopenta[a]phenanthren-3-ol (Compound 7)

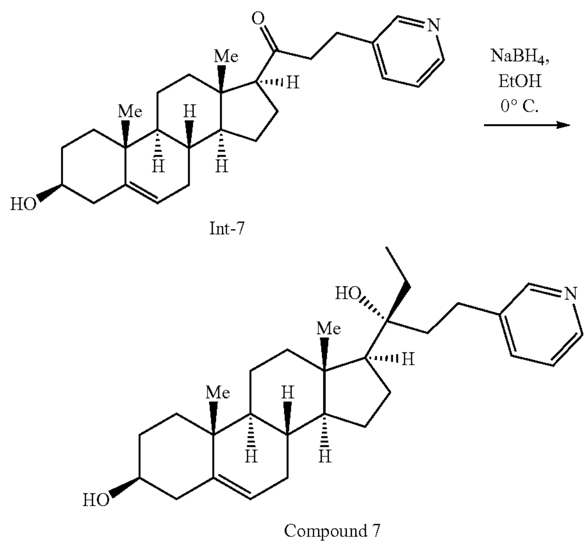

Int-7

Compound 7

Int-7 (0.41 g, 1 mmol) was dissolved in dry tetrahydrofuran (5 mL) at room temperature and cooled to 0° C. under $N_2$-atmosphere. A solution of ethyl magnesium bromide (3 M in ether, 2 mL, 6 mmol) was added dropwise to the reaction mixture at 0° C. The reaction mixture was then stirred at 0° C. for 1 hour until the starting material was mostly consumed (TLC analysis). Then the reaction was carefully quenched with a small volume (~1 mL) of methanol and the mixture further diluted with saturated ammonium chloride solution (20 mL) and dichloromethane (20 mL). The layers were separated, and the aqueous layer extracted with dichloromethane (2×30 mL). The combined organic layers were dried over sodium sulfate, filtered and concentrated in vacuo. The crude mixture was purified via automated chromatography (ISCO) running an ethyl acetate/methanol gradient (0-10%) to yield (3S,8S,9S,10R,13S,14S,17S)-17-((R)-3-hydroxy-1-(pyridin-3-yl)pentan-3-yl)-10,13-dimethyl-2,3,4,7,8,9,10,11,12,13,14,15,16,17-tetradecahydro-1H-cyclopenta[a]phenanthren-3-ol (Compound 7) (0.36 g, 80%). $^{1}$H NMR (400 MHz, $CDCl_3$) δ 8.45 (1H, d, J=1 Hz), 8.42 (1H, dd, J=5, 2 Hz), 7.53-7.48 (1H, m), 7.23-7.18 (1H, m), 5.35-5.31 (1H, m), 3.56-3.45 (1H, m), 2.79-2.63 (2H, m), 2.33-2.17 (2H, m), 2.05 (1H, m), 2.01-1.26 (16H, m), 1.23 (2H, m), 1.18-0.89 (6H, m), 0.98 (3H, s), 0.87 (3H, s); $^{13}$C NMR (100 MHz, $CDCl_3$) δ 149.7, 147.1, 140.8, 138.1, 135.8, 128.6, 123.4, 121.4, 77.2, 71.6, 58.7, 56.9, 50.0, 44.1, 42.9, 42.3, 40.3, 37.2, 36.5, 36.0, 31.7, 31.6, 31.3, 27.5, 23.7, 23.2, 20.9, 19.3, 13.7, 8.4.

Example 9: Synthesis of (3S,5S,8R,9S,10S,13S,14S,17S)-17-((R)-3-hydroxy-1-(pyridin-3-yl)hexan-3-yl)-10,13-dimethylhexadecahydro-1H-cyclopenta[a]phenanthren-3-ol (Compound 14)

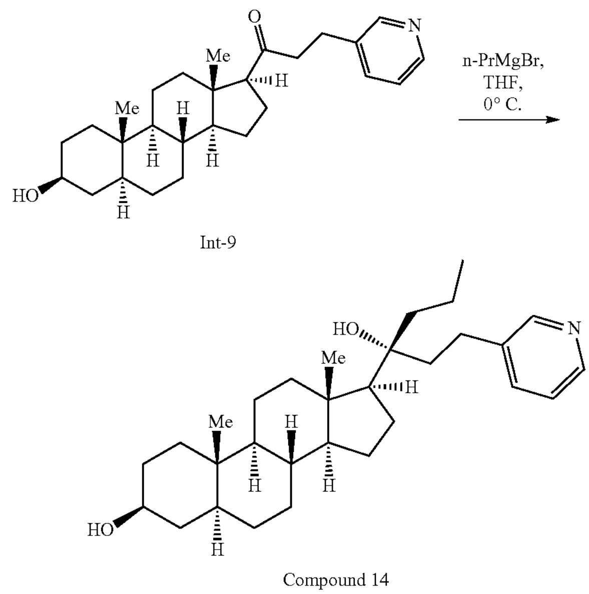

Int-9

Compound 14

Compound 14 was prepared as described in Example 6 by replacing ethyl magnesium bromide with n-propyl magnesium bromide. $^{1}$H NMR (400 MHz, $CDCl_3$) δ 8.42 (2H, brs), 7.52 (1H, m), 7.23 (1H, m), 3.48 (1H, m), 2.74-2.53 (2H, m), 2.00-1.17 (18H, m), 1.15-0.98 (2H, m), 0.97-0.75 (5H, m), 0.84 (3H, s), 0.77 (3H, s), 0.59 (1H, m); $^{13}$C NMR (100 MHz, $CDCl_3$) δ 149.2, 146.7, 138.4, 136.3, 123.6, 77.1, 71.3, 55.9, 54.3, 44.8, 43.1, 41.2, 40.7, 39.5, 38.2, 37.0, 35.5, 34.8, 31.9, 31.6, 31.5, 28.7, 27.4, 23.6, 22.4, 21.1, 14.7, 13.8, 12.3.

Example 10: Synthesis of (3S,8S,9S,10R,13S,14S,17S)-17-((R)-3-hydroxy-1-(pyridinyl)hexan-3-yl)-10,13-dimethyl-2,3,4,7,8,9,10,11,12,13,14,15,16,17-tetradecahydro-1H-cyclopenta[a]phenanthren-3-ol (Compound 15)

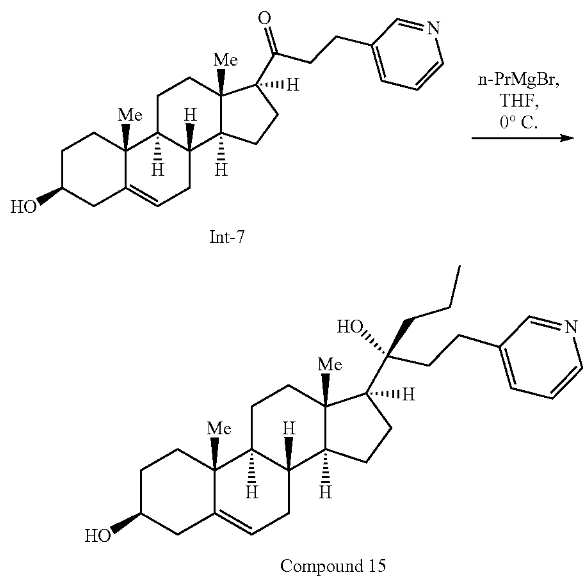

Int-7

Compound 15

Compound 15 was prepared as described in Example 8 by replacing ethyl magnesium bromide with n-propyl magnesium bromide. $^{1}$H NMR (400 MHz, $CDCl_3$) δ 8.41 (2H, brs), 7.52 (1H, m), 7.21 (1H, m), 5.31 (1H, m), 3.48 (1H, m), 2.74-2.53 (3H, m), 2.33-2.12 (2H, m), 2.00-1.74 (5H, m), 1.70-1.35 (8H, m), 1.32-1.18 (3H, m), 1.15-0.81 (m 4H), 0.96 (3H, s), 0.86 (3H, s); $^{13}$C NMR (100 MHz, $CDCl_3$) δ 149.4, 146.9, 141.0, 136.4, 136.1, 123.5, 121.4, 77.0, 73.4, 57.1, 55.8, 50.0, 42.8, 42.3, 41.2, 40.6, 39.5, 37.3, 36.5, 31.8, 31.6, 31.3, 27.4, 23.7, 22.4, 21.1, 20.9, 19.4, 17.3, 14.7, 13.6.

Example 11: Synthesis of (3S,8S,9S,10R,13S,14S,17S)-17-((R)-1-hydroxy-1-phenyl-3-(pyridin-3-yl)propyl)-10,13-dimethyl-2,3,4,7,8,9,10,11,12,13,14,15,16,17-tetradecahydro-1H-cyclopenta[a]phenanthren-3-ol (Compound 16)

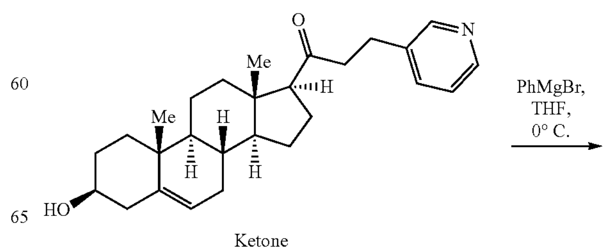

Ketone

-continued

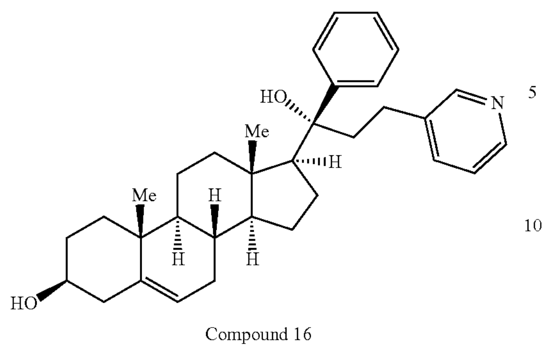

Compound 16

Compound 16 was prepared as described in Example 8 by replacing ethyl magnesium bromide with phenyl magnesium bromide. $^{1}$H NMR (400 MHz, $CDCl_3$) δ 8.42-8.26 (2H, m), 7.43-7.15 (8H, m), 5.31 (1H,$), 3.50 (1H, m), 2.61-1.77 (11H, m), 1.70-1.30 (4H, m), 1.00 (3H, s) 0.92 (3H, s); $^{13}$C NMR (100 MHz, $CDCl_3$) δ 149.1, 146.5, 146.3, 140.9, 138.5, 136.4, 128.1, 126.3, 125.7, 125.1, 123.5, 121.4, 79.3, 71.6, 60.9, 56.9, 50.1, 43.2, 43.1, 43.0, 42.3, 40.5, 37.2, 36.5, 31.7, 31.6, 31.3, 27.6, 25.4, 23.4, 22.8, 20.9, 19.4, 19.3, 13.6.

Example 12: Synthesis of 3-(4-fluorophenyl)-1-((3S,5S,8R,9S,10S,13S,14S,17S)-3-hydroxy-10,13-dimethylhexadecahydro-1H-cyclopenta[a]phenanthren-17-yl)propan-1-one oxime (Compound 17)

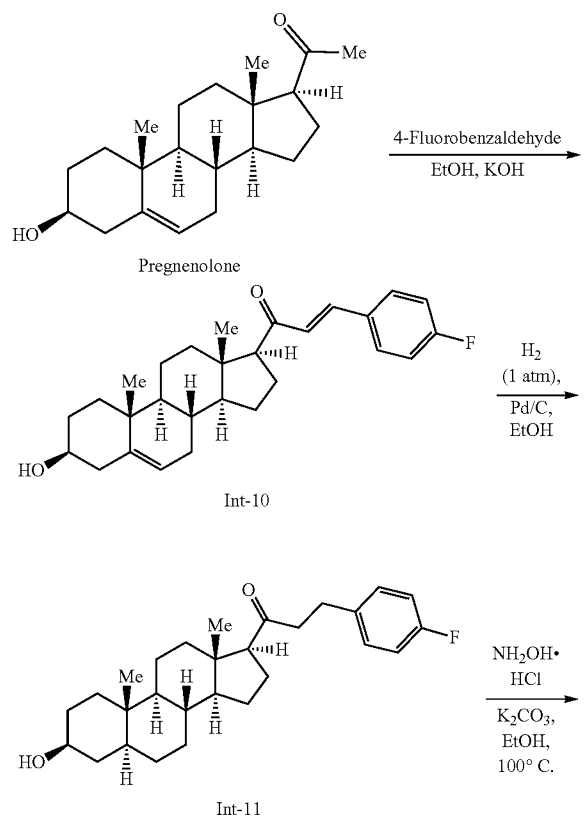

Pregnenolone

Int-10

Int-11

-continued

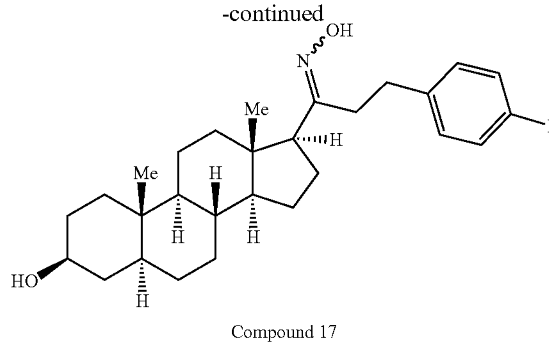

Compound 17

Pregnenolone (6.4 g, 20 mmol) was suspended in ethanol (100 mL) at room temperature. Potassium hydroxide solution (4M, 10 mL, 2 equivalents) was added to the mixture, followed by 4-fluorobenzaldehyde (3 mL, 28 mmol, 1.4 equivalents). The resulting mixture was stirred at room temperature for 24 hours. Upon completion of the reaction (TLC analysis), water (150 mL) was added to precipitate the product. The crude solid product was isolated using vacuum filtration, washed with water (2×70 mL) and then air dried. The crude product was used without further purification to afford Int-10 (8.1 g, 95%). $^{1}$H NMR (400 MHz, $CDCl_3$) δ 7.53 (2H, m), 7.50 (1H, d, J=12 Hz), 7.07 (1H, m), 6.69 (1H, d, J=12 Hz), 5.36 (1H, m), 3.53 (1H, m), 2.83 (1H, t, J=9 Hz), 2.41-2.18 (3H, m), 2.07-1.97 (2H, m), 1.89-1.80 (2H, m), 1.78-1.36 (7H, m), 1.35-1.20 (3H, m), 1.14-1.02 (2H, m), 0.99 (3H, s), 0.63 (3H, s); $^{13}$C NMR (100 MHz, $CDCl_3$) δ 200.2, 163.9 (d, J=252 Hz), 140.8, 140.2, 131.0 (d, J=4 Hz), 130.0 (d, J=8 Hz), 126.4, 121.4, 116.1 (d, J=22 Hz), 71.7, 62.2, 57.2, 50.1, 45.0, 42.3, 39.2, 37.2, 36.2, 32.0, 31.9, 31.6, 24.7, 22.8, 21.1, 19.4, 13.5.

Int-10 (8.0 g, 19 mmol) was dissolved in a mixture of ethanol (50 mL) and ethyl acetate (50 mL) and then palladium on carbon (10% Pd, 0.8 g) was added to the mixture at room temperature. The atmosphere in the reaction flask was purged three times with hydrogen gas using a balloon. The reaction mixture was then stirred at room temperature under a hydrogen atmosphere. After 2 days, the mixture was filtered over celite and concentrated in vacuo to yield the crude ketone (8.0 g). The crude ketone product was dissolved in a minimal volume of hot ethyl acetate (heat gun) and allowed to crystallize overnight. The mother liquor was then removed from the crystalline solid by decantation to afford Int-11 (5.5 g). $^{1}$H NMR (400 MHz, $CDCl_3$) δ 7.12 (2H, m), 6.94 (2H, m), 3.57 (1H, m), 2.84 (2H, m), 2.64 (2H, m), 2.45, (1H, m), 2.14 (1H, m), 1.87 (1H, s), 1.78 (1H, m), 1.74-1.49 (7H, m), 1.44-1.01 (10H, m), 1.01-0.82 (1H, m), 0.78 (3H, s), 0.65 (1H, m), 0.51 (3H); $^{13}$C NMR (100 MHz, $CDCl_3$) δ 210.5, 161.3 (d, J=244 Hz), 137.1 (d, J=3 Hz), 129.8 (d, J=7 Hz), 115.1 (d, J=20 Hz), 71.2, 63.2, 56.8, 54.2, 46.0, 44.8, 44.6, 39.2, 38.1, 37.0, 35.5, 35.5, 32.0, 31.5, 28.9, 28.6, 24.4, 22.9, 21.2, 13.6, 12.3.

Int-11 (0.422 g, 1 mmol) was suspended in ethanol (5 mL) in a pressure vessel and hydroxylamine hydrochloride (0.417 g, 6 mmol) and potassium carbonate (1 g) were added and the vessel was then heated to 100° C. for two hours behind a blast-shield. The solvent was evaporated at reduced pressure and the resulting solid residue was suspended in ethyl acetate (100 mL), washed with water (2×25 mL), dried over $Na_2SO_4$, and the solvent removed under reduced pressure. The crude product was recrystallized from ethanol and the solid collected via filtration to afford 3-(4-fluorophenyl)-1-((3S,5S,8R,9S,10S,13S,14S,17S)-3-hydroxy-10,13-dimethylhexadecahydro-1H-cyclopenta[a]phenanthren-17-yl) propan-1-one oxime (Compound 17) (260 mg). $^{1}H$ NMR (400 MHz, $CDCl_3$) δ 7.15 (2H, m), 6.95 (2H, m), 3.58 (1H, m), 2.94-2.70 (3H, m), 2.39-2.27 (1H, m), 2.19-2.01 (1H, m), 2.00-1.91 (1H, m), 1.86-1.74 (2H, m), 1.73-1.49 (6H, m), 1.46-0.82 (12H, m), 0.79 (3H, s), 0.69-0.57 (1H, m), 0.62 (3H, s); $^{13}C$ NMR (100 MHz, $CDCl_3$) δ 161.8, 161.3 (d, J=244 Hz), 137.1 (d, J=3 Hz), 129.8 (d, J=7 Hz), 115.1 (d, J=20 Hz), 71.3, 56.0, 55.6, 54.3, 44.9, 44.5, 38.8, 38.1, 37.0, 36.7, 32.0, 31.7, 31.4, 30.8, 28.6, 24.1, 23.6, 21.2, 13.6, 12.3.

Example 13: Expression of Hedgehog Target Gene Gli1

The compounds described herein were tested on cell cultures to assess their effects on the mRNA expression of Hedgehog target genes Gli1. Conditioned medium (CM) was collected from CAPAN-1 human pancreatic tumor cells grown to confluence in DMEM containing 10% fetal bovine serum (FBS) and contains Hh proteins that activate the Hh pathway in cells receiving the CM. After 7 days of incubation of confluent cells with the described medium, CM was collected, spun for 5 minutes at 1800 rpm to remove dead cells and debris, and then frozen at −80° C. For treating cells, CM was thawed and diluted 1:2 to 1:6 with DMEM containing 5% FBS. NIH3T3 cells and M2 cells were cultured in 12-well plates with DMEM containing 10% FBS. The cells were then treated with DMEM containing 5% FBS or CM in the presence or absence of the compounds prepared in DMSO when they reach confluence. Quantitative RT-PCR was then performed according to the following approach. After 72 to 96 hours of the treatments, the cells were lysed and subjected to RNA extraction with RNease Plus Min kit (Qiagen). A portion of RNA from each well was subjected to Reverse Transcription (RT) using iScript Reverse Transcription Supermix (BioRad). QPCR was performed to test the expression of Hh target gene Gli1 using IQ SYBR Green Supermix (BioRad).

Figure 6:
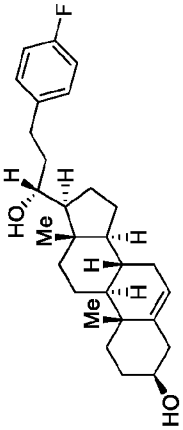
FIG. 6 shows the relative expression of Hedgehog target gene Gli1 in M2 cells treated with Compound 1, Compound 5, or Compound 10. The relative expression (fold) of Gli1 is plotted for Compound 1, Compound 5, and Compound 10, each at concentrations of 1 μM and 5 μM in 5% FBS in DMEM in comparison with a control (DMSO alone).
Figure 6:
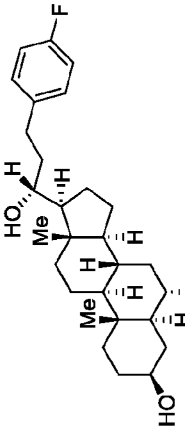
Figure 6:
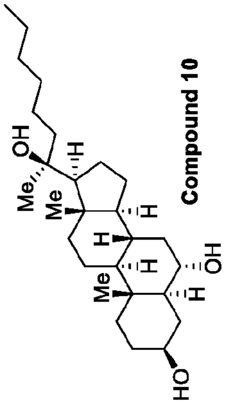
Figure 6:
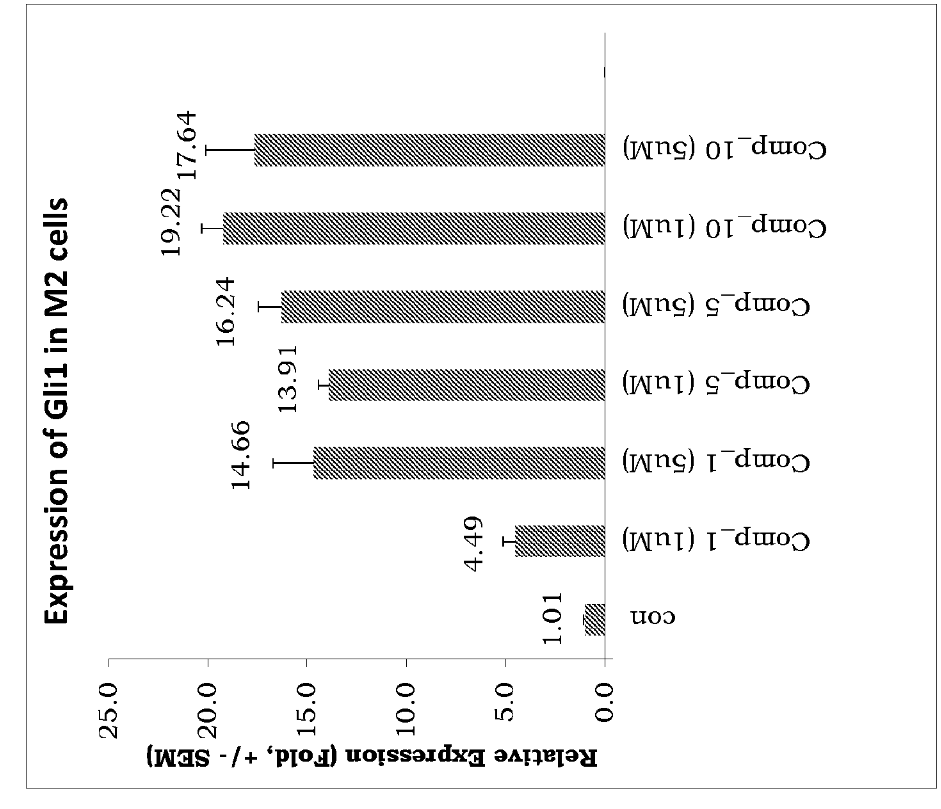

Based on conformational analysis (FIG. 1), C-20 (R)-secondary alcohols are predicted to prefer an extended side chain conformation, as observed in the crystal structure of Compound 5 (FIG. 4). In NIH3T3 cells, Compound 1 and Compound 2 increase Hh signaling, although Compound 2 to a lesser degree than Compound 1 (FIG. 5). In NIH3T3 cells treated with Conditioned Medium (CM, derived from CAPAN-1 cancer cells), Compound 2 is also a weak Hh antagonist. Compound 1, Compound 5, and Compound 10 stimulate Gli signaling in M2 cells (FIG. 6). Contrary to the C-20 (R)-secondary alcohols, conformational analysis of C-20 (R)-tertiary alcohols, like Compounds 6, 7, 11, 12, and 13 are predicted to prefer a bent side chain conformation (FIG. 1), as observed in the crystal structure of Compound 13 (FIG. 2). This is confirmed in the biological data for Compound 6. Compound 6 not only inhibits Gli signaling in NIH3T3 cells treated with CM (FIG. 7) but it also lowers the baseline expression of Gli in NIH3T3 cells (FIG. 8).

Figure 9:
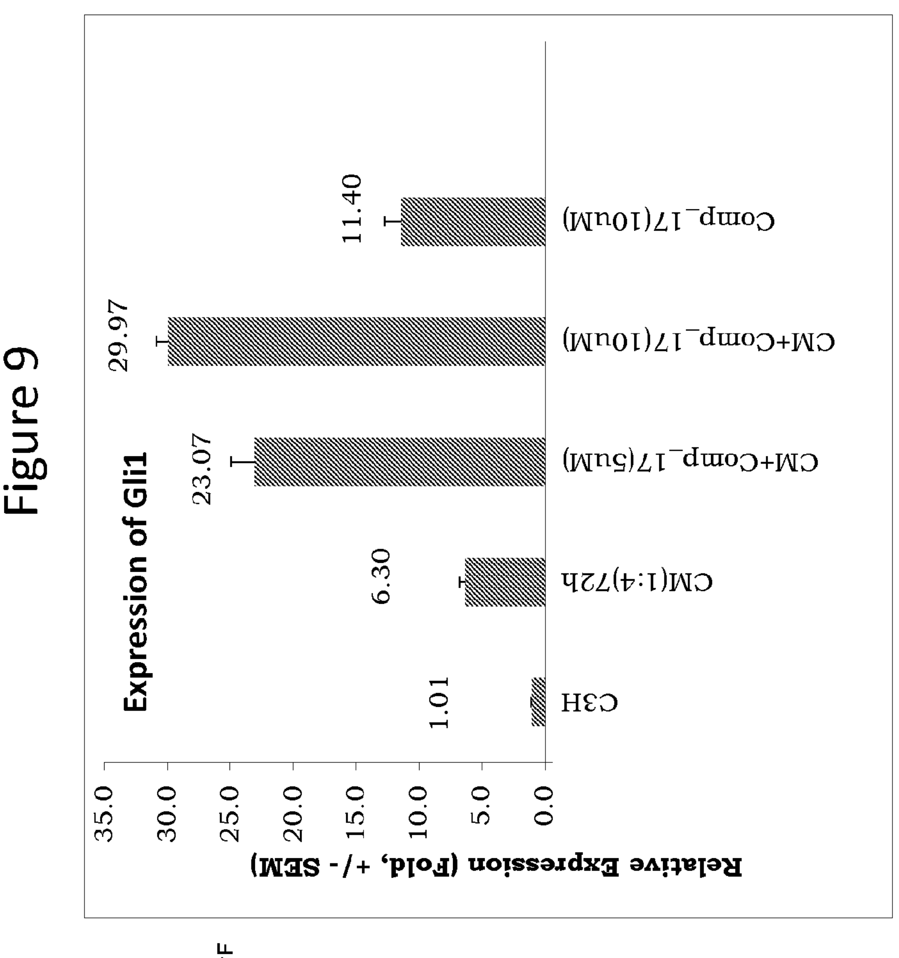
FIG. 9 shows the relative expression of Hedgehog target gene Gli1 in C3H10T1/2 cells treated with Compound 17. The relative expression (fold) of Gli1 is plotted for Compound 17 at concentrations of 5 μM and 10 μM in conditioned medium (CM) or 5% FBS in DMEM in comparison with a control (DMSO alone) and CM.
Figure 9:
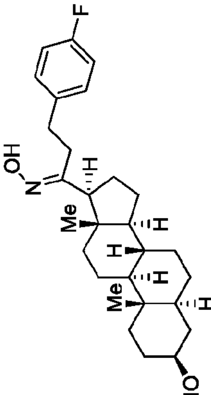

In a similar manner, C3H10T1/2 cells were pretreated for 2 hours with Compound 17 in DMEM containing 5% FBS. Next, cells were treated with CAPAN-1 CM in the absence or presence of Compound 17 at the concentrations as indicated. After 72 hours, RNA was extracted and analyzed by Q-RT-PCR for the expression of Hh target gene Gli1 and normalized to Oaz1 expression. Compound 17 is an activator of Hh signaling and when added together with conditioned medium containing Hh protein activity, it further enhances the conditioned medium induced Gli1 expression (readout for Hh pathway activity) (FIG. 9).

What is claimed is:

1. A compound of Formula (I), or a pharmaceutically acceptable salt or solvate thereof:

Formula (I)

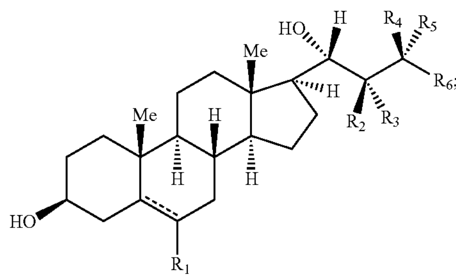

wherein:

------ is a single or double bond;

$R_1$ is hydrogen or —OH;

$R_2$, $R_3$, $R_4$, and $R_5$ are hydrogen;

$R_6$ is $C_6$-$C_{10}$aryl or $C_2$-$C_9$heteroaryl, wherein $C_6$-$C_{10}$aryl or $C_2$-$C_9$heteroaryl are optionally substituted with 1, 2, 3, or 4 $R_7$ groups;

each $R_7$ is independently selected from deuterium, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{2-9}$heteroaryl, —$OR_8$, —$SR_8$, —$N(R_9)(R_{10})$, —C(O)$OR_9$, —C(O)$N(R_9)(R_{10})$, —C(O)$R_{11}$, —S(O)$_2R_{11}$, and —S(O)$_2N(R_9)(R_{10})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR_8$, —$SR_8$, —$N(R_9)(R_{10})$, —C(O)$OR_9$, —C(O)$N(R_9)(R_{10})$, —C(O)$R_{11}$, —S(O)$_2R_{11}$, and —S(O)$_2N(R_9)(R_{10})$;

each $R_8$ is independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl;

each $R_9$ and each $R_{10}$ are each independently selected from H, $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl; and each $R_{11}$ is independently selected from $C_{1-6}$alkyl, $C_{1-6}$haloalkyl, $C_{3-6}$cycloalkyl, $C_{2-9}$heterocycloalkyl, $C_{6-10}$aryl, and $C_{1-9}$heteroaryl.

2. The compound of claim 1 having the structure of Formula (Ia):

Formula (Ia)

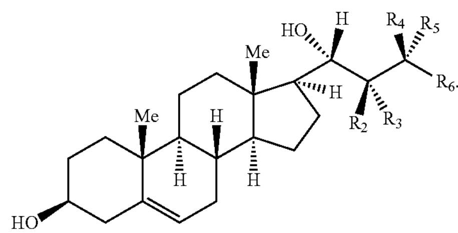

3. The compound of claim 1 having the structure of Formula (Ib):

Formula (Ib)

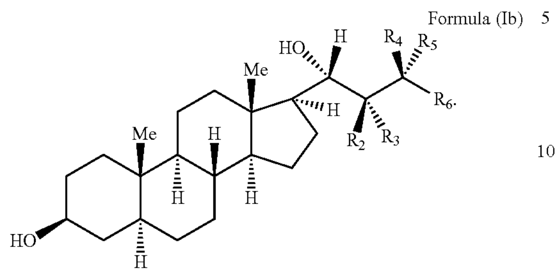

4. The compound of claim 1 having the structure of Formula (Ic):

Formula (Ic)

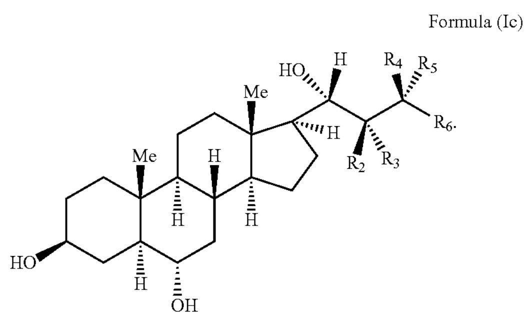

5. The compound of claim 1, wherein $R_6$ is phenyl substituted with 1, 2, or 3 $R_7$ groups.

6. The compound of claim 5, wherein each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy.

7. The compound of claim 6, wherein $R_6$ is phenyl substituted with 1 $R_7$ group and $R_7$ is halogen.

8. The compound of claim 7, wherein $R_6$ is phenyl substituted with 1 $R_7$ group and $R_7$ is fluoro.

9. The compound of claim 6, wherein $R_6$ is phenyl substituted with 1 $R_7$ group and $R_7$ is unsubstituted phenyl.

10. The compound of claim 1, wherein $R_6$ is unsubstituted phenyl.

11. The compound of claim 1, wherein $R_6$ is pyridyl optionally substituted with 1 or 2 $R_7$ groups.

12. The compound of claim 11, wherein each $R_7$ is independently selected from halogen, $C_{1-6}$alkyl, $C_{6-10}$aryl, and $C_{2-9}$heteroaryl, wherein $C_{1-6}$alkyl, $C_{6-10}$aryl, and $C_{2-9}$heteroaryl are optionally substituted with one, two, or three groups independently selected from halogen, oxo, —CN, $C_{1-6}$alkyl, $C_{1-6}$haloalkyl, $C_{1-6}$alkoxy, and $C_{1-6}$haloalkoxy.

13. The compound of claim 1, wherein $R_6$ is unsubstituted pyridyl.

14. A compound, or a pharmaceutically acceptable salt or solvate thereof, having a structure selected from:

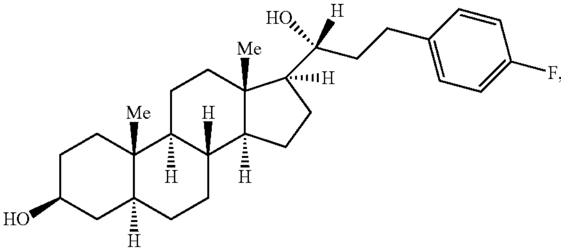

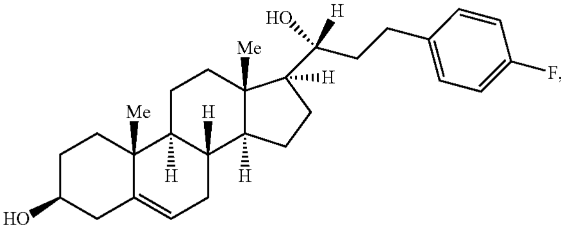

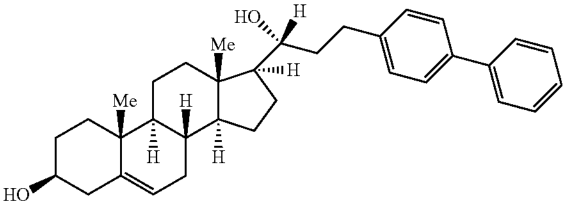

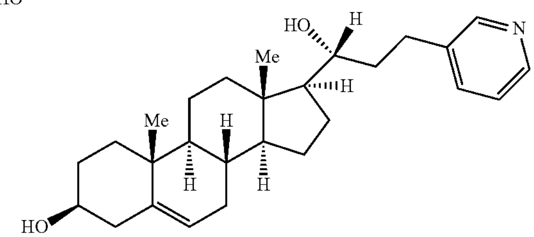

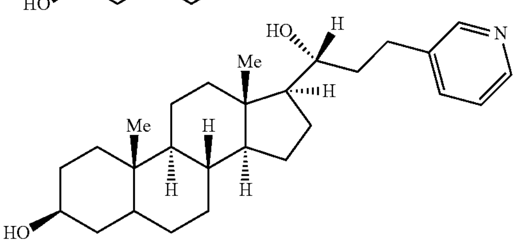

and

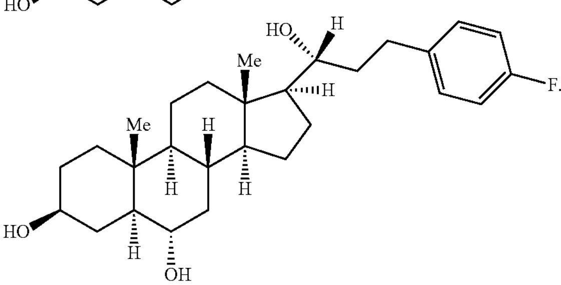

15. A pharmaceutical composition comprising a compound of claim 1 and a pharmaceutically acceptable excipient.

16. A method of modulating Hedgehog signaling in a mammal, comprising administering to the mammal a compound according to claim 1.

17. The method of claim 16, wherein Hedgehog signaling is positively modulated.

18. The method of claim 16, wherein Hedgehog signaling is negatively modulated.

* * * * *